US007344551B2

(12) United States Patent
Barbut et al.

(10) Patent No.: US 7,344,551 B2
(45) Date of Patent: Mar. 18, 2008

(54) CANNULA WITH ASSOCIATED FILTER AND METHODS OF USE DURING CARDIAC SURGERY

(75) Inventors: Denise Barbut, New York, NY (US); Tracy D. Maahs, Redwood City, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 764 days.

(21) Appl. No.: 10/750,701

(22) Filed: Dec. 31, 2003

(65) Prior Publication Data

US 2004/0162576 A1 Aug. 19, 2004

Related U.S. Application Data

(60) Continuation of application No. 10/006,410, filed on Nov. 30, 2001, now Pat. No. 7,011,672, which is a division of application No. 09/691,641, filed on Oct. 18, 2000, now Pat. No. 6,423,086, which is a continuation of application No. 09/455,874, filed on Dec. 6, 1999, now Pat. No. 6,235,045, which is a continuation of application No. 09/336,372, filed on Jun. 17, 1999, now Pat. No. 6,117,154, which is a continuation of application No. 08/842,727, filed on Apr. 16, 1997, now Pat. No. 5,989,281, which is a continuation-in-part of application No. 08/640,015, filed on Apr. 30, 1996, now Pat. No. 5,769,816, which is a continuation-in-part of application No. 08/584,759, filed on Jan. 11, 1996, now abandoned, which is a continuation-in-part of application No. 08/580,223, filed on Dec. 28, 1995, now abandoned, which is a continuation-in-part of application No. 08/553,137, filed on Nov. 7, 1995, now abandoned.

(51) Int. Cl.
*A61B 17/00* (2006.01)

(52) U.S. Cl. ..................................................... 606/200
(58) Field of Classification Search ................ 606/113, 606/114, 159, 127, 200
See application file for complete search history.

(56) References Cited

U.S. PATENT DOCUMENTS 3,472,230 A 10/1969 Fogarty (Continued)

FOREIGN PATENT DOCUMENTS

BR 9301980 10/1993

(Continued)

OTHER PUBLICATIONS

Barbut et al., "Cerebral Emboli Detected During Bypass Surgery Are Associated With Clamp Removal," *Stroke* 25(12):2398-2402 (1994).

(Continued)

*Primary Examiner*—Kevin T. Truong
(74) *Attorney, Agent, or Firm*—Gregory J. Carlin; Rajiv Yadav

(57) ABSTRACT

Devices and methods for filtering blood. The devices generally comprise a mesh for filtering blood flowing within a blood vessel, particularly within an artery such as the aorta, a structure adapted to open and close the mesh within the blood vessel, and a means to actuate the structure. The methods generally include the steps of introducing a mesh into a blood vessel to entrap embolic material, and removing the mesh and the entrapped foreign matter from the blood vessel.

11 Claims, 17 Drawing Sheets

U.S. PATENT DOCUMENTS

| | | | |
|---|---|---|---|
| 3,701,433 | A | 10/1972 | Krakauer et al. |
| 4,425,908 | A * | 1/1984 | Simon .................... 128/899 |
| 4,494,531 | A | 1/1985 | Gianturco |
| 4,572,724 | A | 2/1986 | Rosenberg et al. |
| 4,619,246 | A | 10/1986 | Molgaard-Nielsen et al. |
| 4,688,553 | A | 8/1987 | Metals |
| 4,723,549 | A | 2/1988 | Wholey et al. |
| 4,832,055 | A | 5/1989 | Palestrant |
| 4,873,978 | A | 10/1989 | Ginsburg |
| 4,955,895 | A | 9/1990 | Sugiyama |
| 4,969,891 | A | 11/1990 | Gewertz |
| 5,053,008 | A | 10/1991 | Bajaj |
| 5,133,733 | A | 7/1992 | Rasmussen et al. |
| 5,147,379 | A | 9/1992 | Sabbaghian et al. |
| 5,152,777 | A | 10/1992 | Goldberg et al. |
| 5,160,342 | A | 11/1992 | Reger et al. |
| 5,300,086 | A | 4/1994 | Gory et al. |
| 5,329,942 | A | 7/1994 | Gunther et al. |
| 5,330,451 | A | 7/1994 | Gabbay |
| 5,370,657 | A | 12/1994 | Irie |
| 5,370,685 | A | 12/1994 | Stevens |
| 5,375,612 | A | 12/1994 | Cottenceau et al. |
| 5,383,887 | A | 1/1995 | Nadal |
| 5,415,630 | A | 5/1995 | Gory et al. |
| 5,549,626 | A | 8/1996 | Miller et al. |
| 5,599,329 | A | 2/1997 | Gabbay |
| 5,695,519 | A | 12/1997 | Summers et al. |
| 5,709,704 | A * | 1/1998 | Nott et al. .................... 606/200 |
| 6,179,859 | B1 | 1/2001 | Bates et al. |

FOREIGN PATENT DOCUMENTS

| | | |
|---|---|---|
| DE | 3417738 A1 | 11/1985 |
| EP | 0791340 | 8/1997 |
| FR | 2567405 | 7/1984 |
| SU | 764684 | 9/1980 |
| WO | WO97/17100 | 5/1997 |

OTHER PUBLICATIONS

Barbut et al., "Comparison of Transcranial Doppler Ultrasonography and Transesophageal Echocardiography to Monitor Emboli During Coronary Artery Bypass Surgery," *Stroke* 27(1):87-90 (1996).

Barbut et al., "Aortic Atheromatosis and Risks of Cerebral Embolization," *Journal of Cardiothoracic and Vascular Anesthesia* 10(1):24-30 (1996).

Cascudo et al., "Myxoma of the Right Atrium," *Arquivos Brasileiros de Cardiologia* 56(5):389-391 (1991).

Culliford et al., "The Atherosclerotic Ascending Aorta and Transverse Arch: A New Technique to Prevent Cerebral Injury during Bypass: Experience with 13 Patients," *The Annals of Thoracic Surgery* 41(1):27-35 (1986).

Damásio et al., "Multiple Cerebral Aneurysms and Cardiac Myxoma," *Arch. Neurol.* 32:269-270 (1975).

Da Silva et al., "Postinfarction ventricular septal defect," *J. Thorac. Cardiovasc. Surg.* 97:86-89 (1989).

Da Silva et al., "Heart-lung transplantation. Initial clinical experience," *Arquivos Brasileiros de Cardiologia* 57(2):103-108 (1991).

Da Silva et al., "Heart and Unilateral Lung Transplantation for Cardiomyopathy With High Pulmonary Vascular Resistance," *Ann. Thorac. Surg.* 53:700-702 (1992).

Da Silva et al., "The Heart-lung transplant. Initial clinical experience," *Revista Portuguese de Cardiologia* 12(1):9, 51-5 (1993).

Da Silva et al., "Heterotopic heart transplantation: A direct pulmonary artery anastomosis technique," *The Journal of Thoracic and Cardiovascular Surgery* 108(4):795 (1994).

Fornari et al., "High-resolution electrocardiogram in the study of early rejection of heart transplant by spectral temporal mapping," *Arquivos Brasileiros de Cardiologia* 60(3):183-185 (1993).

Lazor et al., "Use of the Multiple Uptake Gated Acquisition Scan for the Preoperative Assessment of Cardiac Risk," *Surgery, Gynecology & Obstetrics* 167:234-238 (1988).

Mills et al., "Atherosclerosis of the ascending aorta and coronary artery bypass," *J. Thoracic Cardiovasc. Surg.* 102(4):546-553 (1991).

Schneider, "Particulate Emboli Retained by Bypass Blood Filters," *Scand. J. Haemat.* 12:185-203 (1974).

Van Der Linden et al., "When Do Cerebral Emboli Appear During Open Heart Operations? A Transcranial Doppler Study," *Ann. Thorac. Surg.* 51:237-241 (1991).

Yao et al., "Detection of Aortic Emboli by Transesophageal Echocardiography During Coronary Bypass Surgery," ASA Abstract No. 126, *Anesthesiology* 83(3) (1995).

* cited by examiner

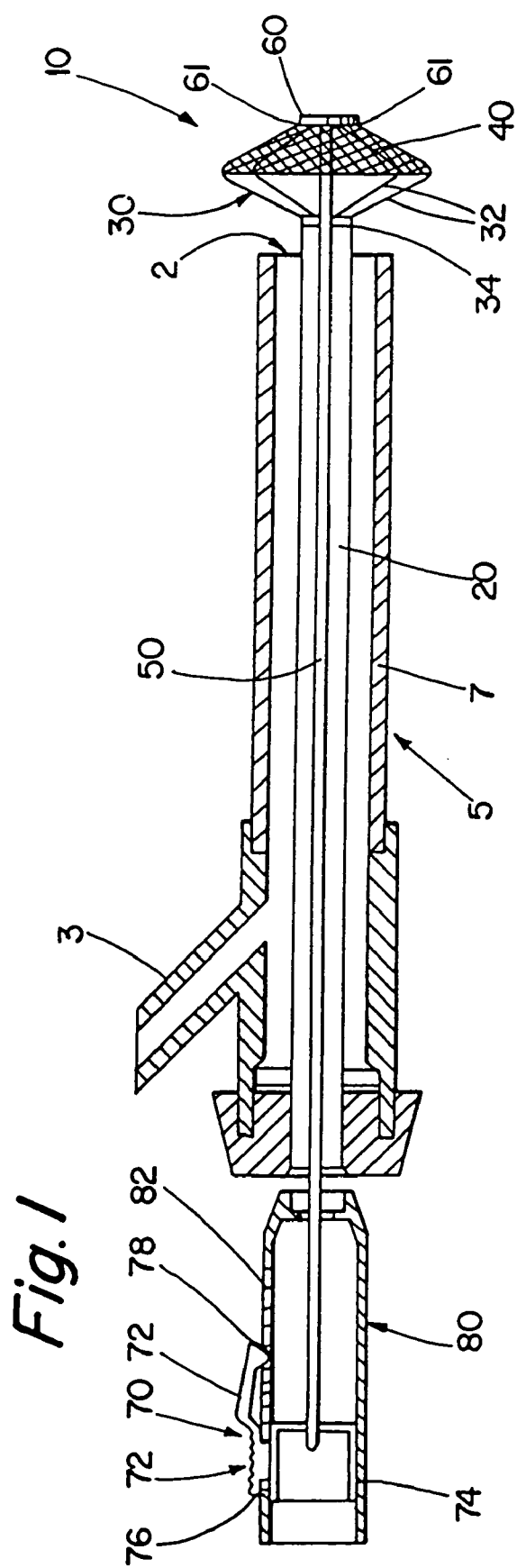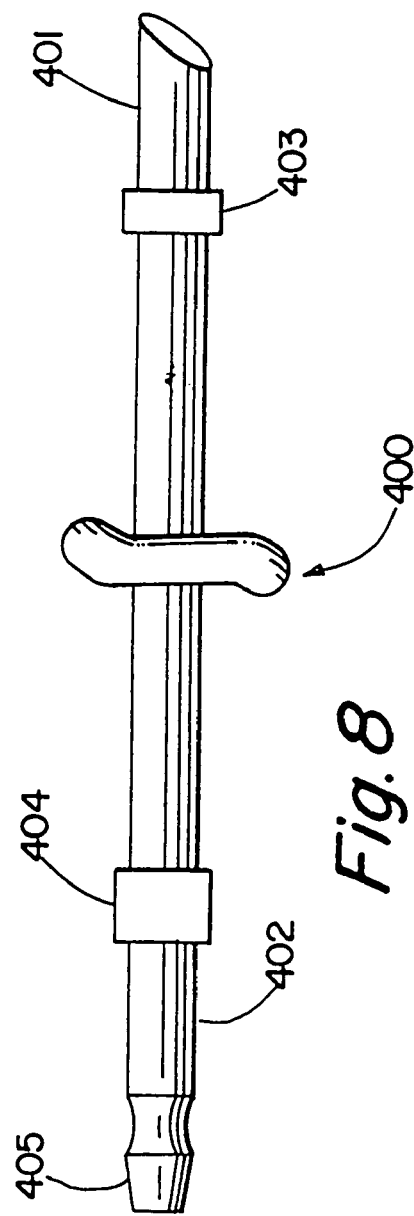

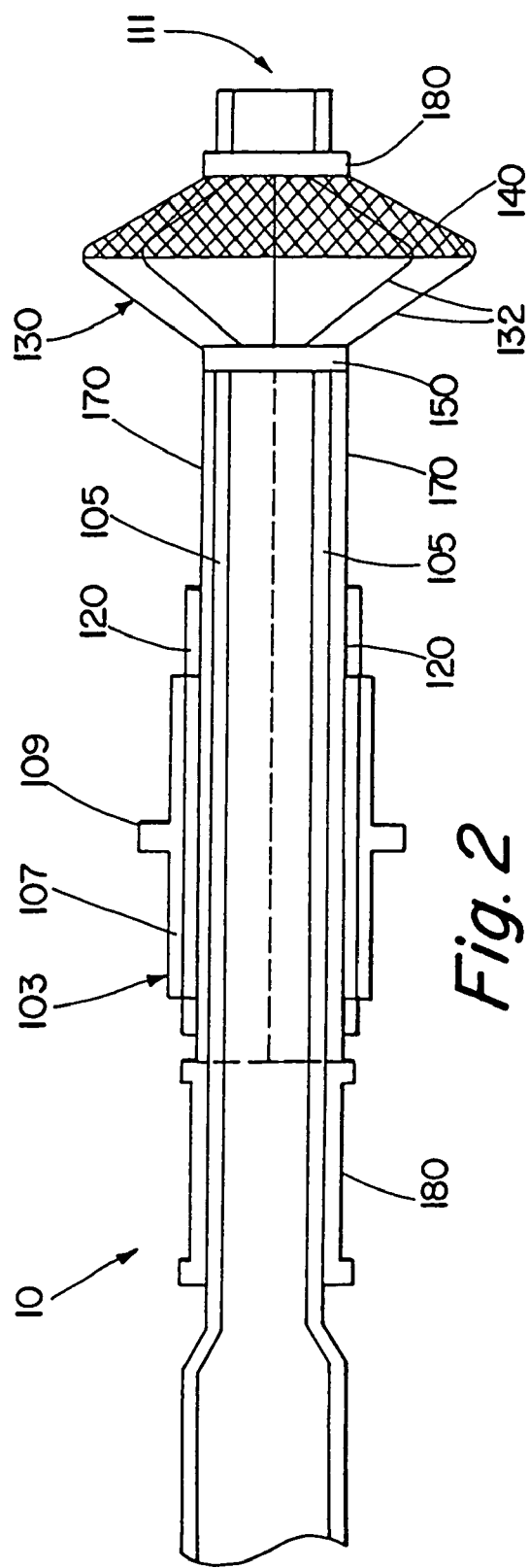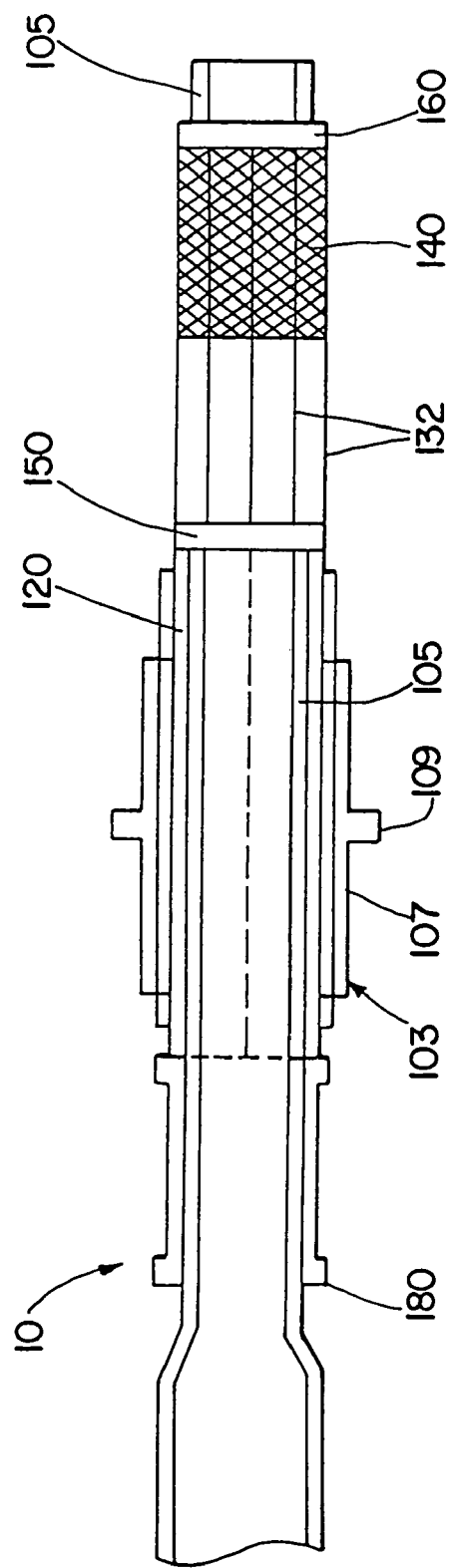

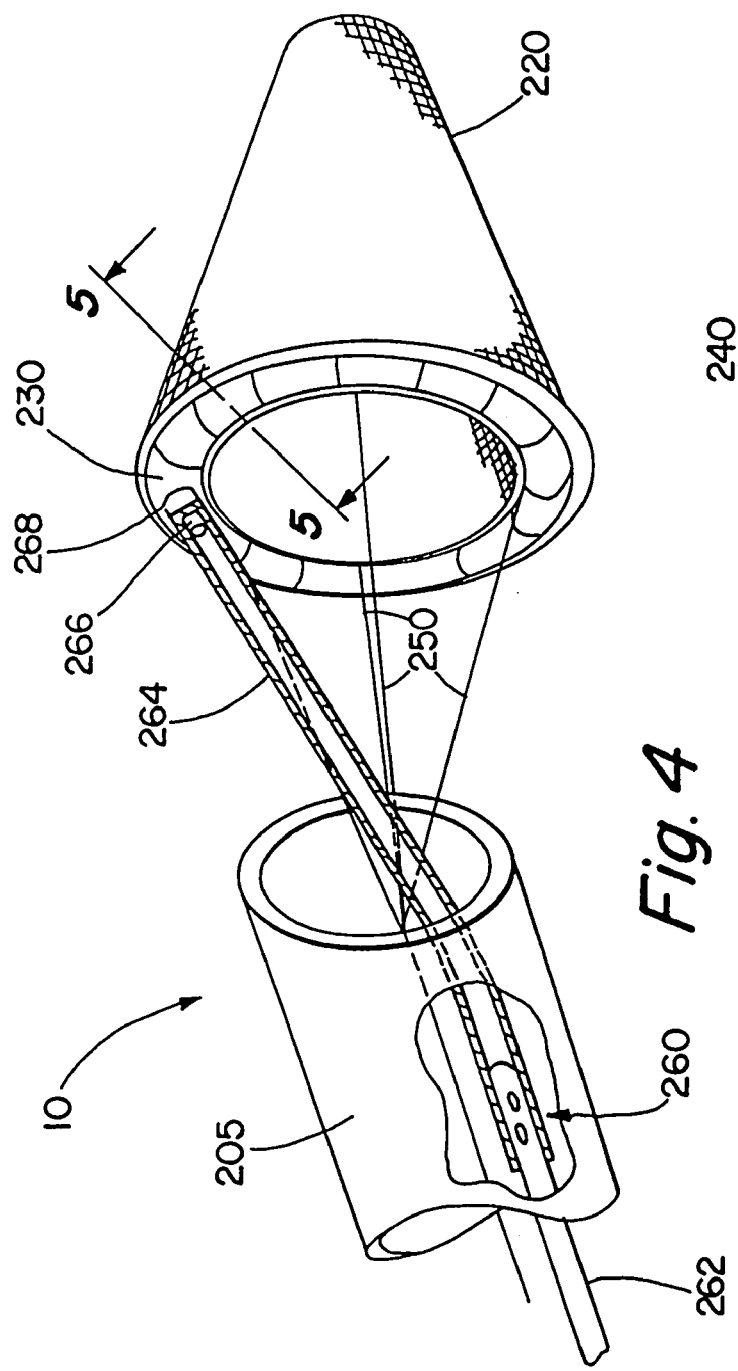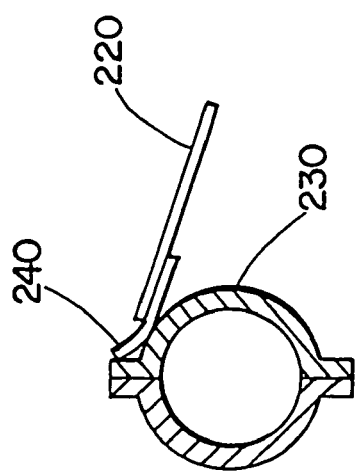
Fig. 4
Fig. 5

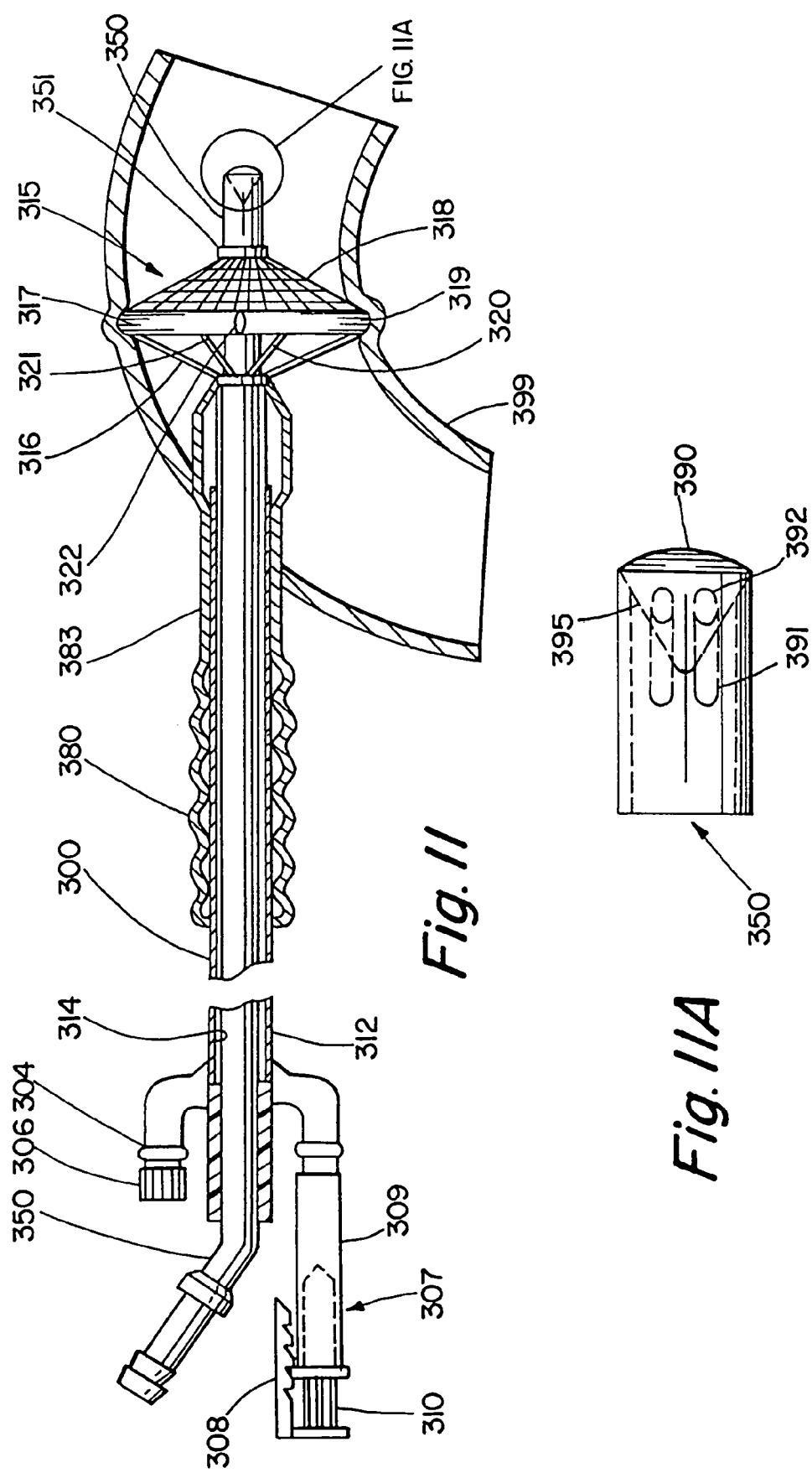

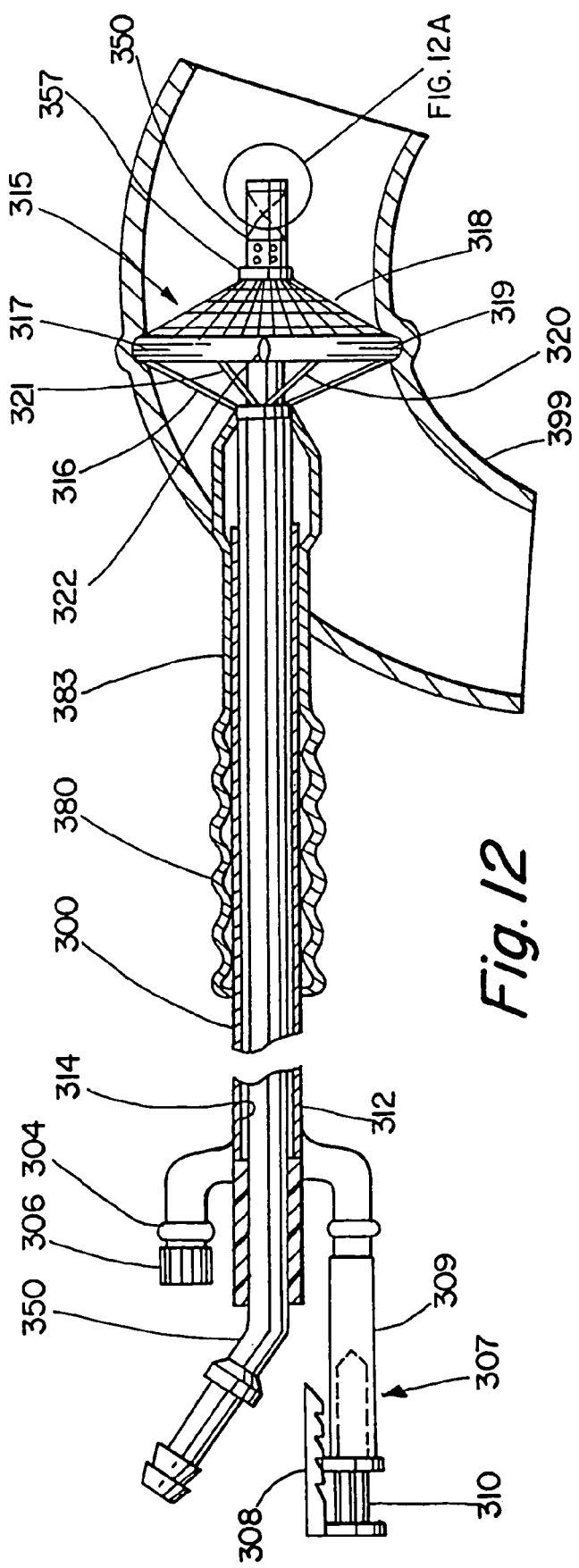
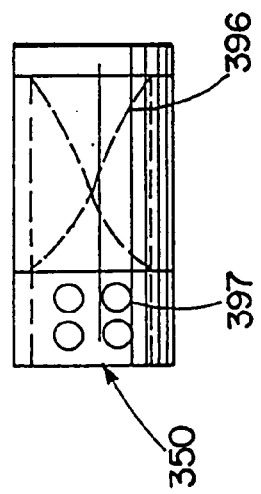
Fig. 12
Fig. 12A

CANNULA WITH ASSOCIATED FILTER AND METHODS OF USE DURING CARDIAC SURGERY

This is a continuation of U.S. application Ser. No. 10/006,410, filed Nov. 30, 2001 now U.S. Pat. No. 7,011,672, which is a division of U.S. application Ser. No. 09/691,641, filed Oct. 18, 2000, now U.S. Pat. No. 6,423,086, which is a continuation of U.S. application Ser. No. 09/455,874, filed Dec. 6, 1999, now U.S. Pat. No. 6,235,045, which is a continuation of U.S. application Ser. No. 09/336,372, filed Jun. 17, 1999, now U.S. Pat. No. 6,117,154, which is a continuation of U.S. application Ser. No. 08/842,727, filed Apr. 16, 1997, now U.S. Pat. No. 5,989,281, which is a continuation-in-part of U.S. application Ser. No. 08/640,015, filed Apr. 30, 1996, now U.S. Pat. No. 5,769,816, which is a continuation-in-part of U.S. application Ser. No. 08/584,759, filed Jan. 11, 1996, now abandoned, which is a continuation-in-part of U.S. application Ser. No. 08/580,223, filed Dec. 28, 1995, now abandoned, which is a continuation-in-part of U.S. application Ser. No. 08/553,137, filed Nov. 7, 1995, now abandoned. Each of the above-identified applications and patents are expressly incorporated herein by reference in their entirety.

FIELD OF THE INVENTION

The present invention relates generally to blood filter devices for temporary placement in a blood vessel to capture embolic material, and more particularly to a cannula device having an associated blood filter for placement in a blood vessel to carry blood to an artery from a bypass-oxygenator system and to entrap embolic material in the vessel. More particularly, the invention relates to a blood filter device to be placed in the aorta during cardiac surgery. The present invention also relates to methods for temporarily filtering blood to entrap and remove embolic material and, more particularly, to methods for protecting a patient from embolization which has been caused by procedures such as incising, clamping, and clamp release which can dislodge atheromatous material from the artery.

BACKGROUND OF THE INVENTION

There are a number of known devices designed to filter blood. The vast majority of these devices are designed for permanent placement in veins, in order to trap emboli destined for the lungs. For example, Kimmell, Jr., U.S. Pat. No. 3,952,747 (this and all other references cited herein are expressly incorporated by reference as if fully set forth in their entirety herein), discloses the so-called Kimray-Greenfield filter. This is a permanent filter typically placed in the vena cava comprising a plurality of convergent legs in a generally conical array, which are joined at their convergent ends to an apical hub. Each leg has a bent hook at its end to impale the internal walls of the vena cava.

Cottenceau et al., U.S. Pat. No. 5,375,612, discloses a blood filter intended for implantation in a blood vessel, typically in the vena cava. This device comprises a zig-zagged thread wound on itself and a central strainer section to retain blood clots. This strainer section comprises a meshed net and may be made from a biologically absorbable material. This device is also provided with attachment means which penetrate into the wall of the vessel.

Gunther et al., U.S. Pat. No. 5,329,942, discloses a method for filtering blood in the venous system wherein a filter is positioned within a blood vessel beyond the distal end of a catheter by a positioning means guided through the catheter. The positioning means is locked to the catheter, and the catheter is anchored to the patient. The filter takes the form of a basket and is comprised of a plurality of thin resilient wires. This filter can be repositioned within the vessel to avoid endothelialization within the vessel wall.

Similarly, Lefebvre, French Patent No. 2,567,405, discloses a blood filter for implantation by an endovenous route into the vena cava. The filter is present in the form of a cone, and the filtering means may consist of a flexible metallic grid, or a flexible synthetic or plastic grid, or a weave of synthetic filaments, or a non-degradable or possibly biodegradable textile cloth. In order to hold the filter within the vein, this device includes flexible rods which are sharpened so that they may easily penetrate into the inner wall of the vena cava.

There are various problems associated with permanent filters. For example, when a filter remains in contact with the inner wall of the vena cava for a substantial period of time, endothelialization takes place and the filter will subsequently become attached to the vena cava. This endothelialization may cause further occlusion of the vessel, thereby contributing to the problem the filter was intended to solve. Except for the Gunther device, these prior art filters do not address this problem.

A temporary venous filter device is disclosed in Bajaj, U.S. Pat. No. 5,053,008. This device treats emboli in the pulmonary artery which, despite its name, is in fact a vein. The Bajaj device is an intracardiac catheter for temporary placement in the pulmonary trunk of a patient predisposed to pulmonary embolism because of hip surgery, stroke or cerebral hemorrhage, major trauma, major abdominal or pelvic surgery, neurosurgery, neoplasm, sepsis, cardiorespiratory failure or immobilization.

The Bajaj device includes an umbrella made from meshwork which traps venous emboli before they reach the lungs. This device can also lyse emboli with a thrombolytic agent such as tissue plasminogen activator (TPA), destroy emboli with high velocity ultrasound energy, and remove emboli by vacuum suction through the lumen of the catheter. This very complex device is designed for venous filtration and is difficult to justify when good alternative treatments exist.

There are very few intravascular devices designed for arterial use. A filter that functions not only in veins, but also in arteries must address additional concerns because of the hemodynamic differences between arteries and veins. Arteries are much more flexible and elastic than veins and, in the arteries, blood flow is pulsatile with large pressure variations between systolic and diastolic flow. These pressure variations cause the artery walls to expand and contract. Blood flow rates in the arteries vary from about 1 to about 5 L/min.

Ginsburg, U.S. Pat. No. 4,873,978, discloses an arterial device. This device includes a catheter that has a strainer device at its distal end. This device is normally used in conjunction with non-surgical angioplastic treatment. This device is inserted into the vessel downstream from the treatment site and, after the treatment, the strainer is collapsed around the entrapped emboli, and the strainer and emboli are removed from the body. The Ginsburg device could not withstand flow rates of 5 L/min. It is designed for only small arteries and therefore could not capture emboli destined for all parts of the body. For example, it would not catch emboli going to the brain.

Ing. Walter Hengst GmbH & Co, German Patent DE 34 17 738, discloses another filter which may be used in the arteries of persons with a risk of embolism. This filter has an inherent tension which converts the filter from the collapsed to the unfolded state, or it can be unfolded by means of a folding linkage system. This folding linkage system comprises a plurality of folding arms spaced in parallel rows along the longitudinal axis of the conical filter (roughly similar to branches on a tree). The folding arms may be provided with small barbs at their projecting ends intended to penetrate the wall of the blood vessel to improve the hold of the filter within the vessel.

Moreover, da Silva, Brazil Patent Application No. PI9301980A, discusses an arterial filter for use during certain heart operations where the left chamber of the heart is opened. The filter in this case is used to collect certain particles not removed on cleaning the surgical site.

What is needed is a simple, safe blood filter for temporary use. For example, a temporary arterial device for use during surgery that neither complicates nor lengthens the surgical procedure would be desirable. Existing prior art devices are inadequate for this purpose.

SUMMARY OF THE INVENTION

The present invention relates to blood filter devices and methods of filtering blood. The devices of the present invention are adapted to filter embolic material from the blood. Embolic material or foreign matter is any particulate matter which may cause complications in the body if allowed to travel freely in the bloodstream. This particulate matter includes but is not limited to atheromatous fragments or material, and fat.

In one embodiment, the device includes four major elements: a mesh, which filters blood flowing in a blood vessel; an insertion tube adapted for placing the mesh into and removing it from the blood vessel; an umbrella frame adapted for connecting the mesh to the insertion tube and for positioning and maintaining the mesh in a position wherein blood passes therethrough; and a means for opening and closing the umbrella frame.

In another embodiment, the device includes three major elements: a mesh, which filters blood flowing in a blood vessel; an umbrella frame adapted for positioning and maintaining the mesh in a position wherein blood passes therethrough; and a means for opening and closing the umbrella frame. The umbrella frame is affixed to a cannula which is inserted into the blood vessel. In alternative embodiments, the mesh additionally may be provided to cover the end of the cannula if necessary. This additional mesh simply may be an extension of the mesh of the second preferred embodiment, or it may be a separate mesh located either at the end of the cannula or within the cannula.

In another embodiment, the device includes four major elements: a continuous mesh for filtering blood flowing within a blood vessel; an inflatable donut-shaped balloon adapted to open and close the mesh; a plurality of tie lines to hold the mesh and balloon in place within the bloodstream; and an actuation assembly. In a preferred embodiment, the mesh is cone-shaped and four tie lines attached to the inflatable balloon are employed to hold the balloon and the mesh in place for filtering.

In still another embodiment, the device may include an arterial cannula disposed within a pressurizing cannula. The pressurizing cannula has a proximal region, a distal region, and an intermediate region therebetween, which intermediate region includes a first lumen passing from the proximal to distal end and shaped to receive a cannula for blood supply. The distal region may include an associated filter comprising a mesh which may have a substantially conical shape in an expanded condition and which may be contracted to a smaller, substantially cylindrical shape. The proximal end of the mesh may be attached to an inflatable, donut-shaped balloon or inflation seal adapted to open and close the mesh. The inflation seal-mesh assembly may be attached at its proximal end to the pressurizing cannula and, at its distal end, may optionally include any of an unbroken continuous mesh, a mesh attached to a distal region of the cannula for blood supply, and a mesh attached to a distal region of the pressurizing cannula. The pressurizing cannula will generally include means for inflating and deflating the inflation seal.

In another embodiment, the device includes a mesh, an arterial cannula, a blood flow diffuser and a structure adapted to open and close the mesh within the blood vessel, such as an umbrella frame or inflatable balloon. The blood flow diffuser may be located inside or outside of the arterial cannula. In both the intra-cannula and extra-cannula diffuser embodiments, the flow diffuser can be located either proximal or distal to the mesh.

In another embodiment, the device includes a sleeve which, when unrolled, captures the mesh and the expansion frame adapted to open and close the mesh. In one embodiment the sleeve may be actuated by control lines which control the unrolling and rolling-up of the sleeve. The captured structure may be an umbrella frame adapted for positioning and maintaining the mesh in a position wherein blood passes therethrough. Alternatively, the captured structure is an inflatable balloon.

In still another embodiment, the device includes a cannula made in part of a deformable (e.g.) elastomeric material such that the deformable part of the cannula collapses to absorb the mesh and the corresponding adapted structure upon mesh closure, thereby reducing the profile of the instrument for vessel introduction.

The methods of the present invention relate to filtering blood flowing within a blood vessel, particularly to entrap embolic material, thereby protecting a patient from embolization. In accordance with one aspect of the method of the invention, a patient is protected from embolization during surgery while performing a procedure affecting a region of an artery of the patient wherein the artery includes foreign matter on an inside surface thereof at least a portion of which is dislodged as a result of mechanical or other forces applied during the procedure, by deploying a removable filtration device in a blood vessel downstream of one affected region of the artery to entrap the dislodged foreign matter.

In other embodiments, the methods of the present invention generally include the following steps: introducing a mesh into a blood vessel to entrap embolic material or foreign matter in the blood, positioning the mesh, if necessary, and removing the mesh and the entrapped foreign matter from the blood vessel. Additionally, visualization techniques including transcranial doppler ultrasonography, transesophageal echocardiography, epicardiac echocardiography, and transcutaneous or intravascular ultrasonography in conjunction with the procedure may be used to ensure effective filtration.

In a preferred method, blood is filtered during cardiac surgery, in particular during cardiac bypass surgery, to protect a patient from embolization. In this method, the mesh is positioned in the aorta where it filters blood before it reaches the carotid arteries, brachiocephalic trunk, and left subclavian artery.

The present invention was developed, in part, in view of a recognition of the occurrence of embolization during cardiac surgery. Emboli are frequently detected in cardiac surgery patients and have been found to account for neurologic, cardiac and other systemic complications. Specifically, embolization appears to contribute significantly to problems such as strokes, lengthy hospital stays and, in some cases, death. Of the patients undergoing cardiac surgery, 5-10% experience strokes and 30% become cognitively impaired. In addition, it has been recognized that embolization is often the result of procedures performed on blood vessels such as incising, clamping, and cannulation, wherein mechanical or other force is applied to the vessel. See, for example, Barbut et al., "Cerebral Emboli Detected During Bypass Surgery Are Associated With Clamp Removal," *Stroke,* 25(12):2398-2402 (1994), which is incorporated herein by reference in its entirety. These procedures are commonly performed in many different types of surgery including cardiac surgery, coronary artery surgery including coronary artery bypass graft surgery, aneurysm repair surgery, angioplasty, atherectomy, and endarterectomy, including carotid endarterectomy. It has also been recognized that reintroducing blood into blood vessels with a cannula during these procedures can dislodge plaque and other emboli-creating materials as a result of blood impinging upon the vessel wall at high velocities. See, for example, Cosgrove et. al., Low Velocity Aortic Cannula, U.S. Pat. No. 5,354,288. Finally, it has been found that the occurrence of embolization is more likely in certain types of patients. For example, embolization occurs more frequently in elderly patients and in those patients who have atheromatosis. In fact, atheromatous embolization, which is related to severity of aortic atheromatosis, is the single most important contributing factor to perioperative neurologic morbidity in patients undergoing cardiac surgery.

Embolic material, which has been detected at 2.88 mm in diameter, will generally range from 0.02 mm (20 µm) to 5 mm, and consists predominantly of atheromatous fragments dislodged from the aortic wall and air bubbles introduced during dissection, but also includes platelet aggregates which form during cardiac surgery. See Barbut et al., "Determination of Embolic Size and Volume of Embolization During Coronary Artery Bypass Surgery Using Transesophageal Echocardiography," *J Cardiothoracic Anesthesia* (1996). These emboli enter either the cerebral circulation or systemic arterial system. Those entering the cerebral circulation obstruct small arteries and lead to macroscopic or microscopic cerebral infarction, with ensuing neurocognitive dysfunction. Systemic emboli similarly cause infarction, leading to cardiac, renal, mesenteric, and other ischemic complications. See Barbut et al., "Aortic Atheromatosis And Risks of Cerebral Embolization," *Journal of Cardiothoracic and Vascular Anesthesia* 10(1):24-30 (1996), which is incorporated herein by reference in its entirety.

Emboli entering the cerebral circulation during coronary artery bypass surgery have been detected with transcranial Doppler ultrasonography (TCD). TCD is a standard visualization technique used for monitoring emboli in the cerebral circulation. To detect emboli using TCD, the middle cerebral artery of a bypass patient is continuously monitored from aortic cannulation to bypass discontinuation using a 2 MHZ pulsed-wave TCD probe (Medasonics-CDS) placed on the patient's temple at a depth of 4.5 to 6.0 cm. The number of emboli is determined by counting the number of embolic signals, which are high-amplitude, unidirectional, transient signals, lasting less than 0.1 second in duration and associated with a characteristic chirping sound.

TCD is useful in analyzing the relationship between embolization and procedures performed on blood vessels. For example, the timing of embolic signals detected by TCD have been recorded along with the timing of procedures performed during open or closed cardiac surgical procedures. One of these procedures is cross-clamping of the aorta to temporarily block the flow of blood back into the heart. It has been found that flurries of emboli are frequently detected after aortic clamping and clamp release. During the placement and removal for the clamps, atheromatous material along the aortic wall apparently becomes detached and finds its way to the brain and other parts of the body. Similarly, flurries of emboli are also detected during aortic cannulation and inception and termination of bypass.

Transesophageal echocardiography (TEE), another standard visualization technique known in the art, is significant in the detection of conditions which may predispose a patient to embolization. TEE is an invasive technique, which has been used, with either biplanar and multiplanar probes, to visualize segments of the aorta, to ascertain the presence of atheroma. This technique permits physicians to visualize the aortic wall in great detail and to quantify atheromatous aortic plaque according to thickness, degree of intraluminal protrusion and presence or absence of mobile components, as well as visualize emboli within the vascular lumen. See, for example, Barbut et al., "Comparison of Transcranial Doppler and Transesophageal Echocardiography to Monitor Emboli During Coronary Bypass Surgery," *Stroke* 27(1):87-90 (1996) and Yao, Barbut et al., "Detection of Aortic Emboli By Transesophageal Echocardiography During Coronary Artery Bypass Surgery," *Journal of Cardiothoracic Anesthesia* 10(3):314-317 (May 1996), and *Anesthesiology* 83(3A):A126 (1995), which are incorporated herein by reference in their entirety. Through TEE, one may also determine which segments of a vessel wall contain the most plaque. For example, in patients with aortic atheromatous disease, mobile plaque has been found to be the least common in the ascending aorta, much more common in the distal arch and most frequent in the descending segment. Furthermore, TEE-detected aortic plaque is unequivocally associated with stroke. Plaque of all thickness is associated with stroke but the association is strongest for plaques over 4 mm in thickness. See Amarenco et al., "Atherosclerotic disease of the aortic arch and the risk of ischemic stroke," *New England Journal of Medicine,* 331:1474-1479 (1994).

Another visualization technique, intravascular ultrasound, is also useful in evaluating the condition of a patient's blood vessel. Unlike the other techniques mentioned, intravascular ultrasound visualizes the blood vessel from its inside. Thus, for example, it is useful for visualizing the ascending aorta overcoming deficiencies of the other techniques. In one aspect of the invention, it is contemplated that intravascular ultrasound is useful in conjunction with devices disclosed herein. In this way, the device and visualizing means may be introduced into the vessel by means of a single catheter.

Through visualization techniques such as TEE epicardial aortic ultrasonography and intravascular ultrasound, it is possible to identify the patients with plaque and to determine appropriate regions of a patient's vessel on which to perform certain procedures. For example, during cardiac surgery, in particular, coronary artery bypass surgery, positioning a probe to view the aortic arch allows monitoring of all sources of emboli in this procedure, including air introduced during aortic cannulation, air in the bypass equipment, platelet emboli formed by turbulence in the system and atheromatous emboli from the aortic wall. Visualization techniques may be used in conjunction with a blood filter device to filter blood effectively. For example, through use of a visualization technique, a user may adjust the position of a blood filter device, and the degree of actuation of that device as well as assessing the efficacy of the device by determining whether foreign matter has bypassed the device.

It is an object of the present invention to eliminate or reduce the problems that have been recognized as relating to embolization. The present invention is intended to entrap and remove emboli in a variety of situations. For example, in accordance with one aspect of the invention, blood may be filtered in a patient during procedures which affect blood vessels of the patient. The present invention is particularly suited for temporary filtration of blood in an artery of a patient to entrap embolic debris. This in turn will eliminate or reduce neurologic, cognitive, and cardiac complications helping to reduce length of hospital stay. In accordance with another aspect of the invention, blood may be filtered temporarily in a patient who has been identified as being at risk for embolization.

As for the devices, one object is to provide simple, safe and reliable devices that are easy to manufacture and use. A further object is to provide devices that may be used in any blood vessel. Yet another object is to provide devices that will improve surgery by lessening complications, decreasing the length of patients' hospital stays and lowering costs associated with the surgery. See Barbut et al., "Intraoperative Embolization Affects Neurologic and Cardiac Outcome and Length of Hospital Stay in Patients Undergoing Coronary Bypass Surgery," *Stroke* (1996).

The devices disclosed herein have the following characteristics: can withstand high arterial blood flow rates for an extended time; include a mesh that is porous enough to allow adequate blood flow in a blood vessel while capturing mobile emboli; can be used with or without imaging equipment; remove the entrapped emboli when the operation has ended; will not dislodge mobile plaque; and can be used in men, women, and children of varying sizes.

As for methods of use, an object is to provide temporary filtration in any blood vessel and more particularly in any artery. A further object is to provide a method for temporarily filtering blood in an aorta of a patient before the blood reaches the carotid arteries and the distal aorta. A further object is to provide a method for filtering blood in patients who have been identified as being at risk for embolization. Yet a further object is to provide a method to be carried out in conjunction with a blood filter device and visualization technique that will assist a user in determining appropriate sites of filtration. This visualization technique also may assist the user in adjusting the blood filter device to ensure effective filtration. Yet a further object is to provide a method for filtering blood during surgery only when filtration is necessary. Yet another object is to provide a method for eliminating or minimizing embolization resulting from a procedure on a patient's blood vessel by using a visualization technique to determine an appropriate site to perform the procedure. Another object is to provide a method for minimizing incidence of thromboatheroembolisms resulting from cannula procedures by coordinating filtration and blood flow diffusion techniques in a single device. Another object is to provide a method of passing a filtering device through a vessel wall by first capturing the mesh filter with a sleeve so as to reduce the device profile. For a related discussion of subject matter pertaining to a filter cannula, the reader is referred to co-pending U.S. application Ser. No. 08/640,015, filed Apr. 30, 1996, U.S. application Ser. No. 08/584,759, filed Jan. 9, 1996, U.S. application Ser. No. 08/580,223, filed Dec. 28, 1995, and U.S. application Ser. No. 08/553,137, filed Nov. 7, 1995, all of which are expressly incorporated herein by reference in their entirety.

BRIEF DESCRIPTION OF DRAWINGS

Reference is next made to a brief description of the drawings, which are intended to illustrate blood filter devices for use herein. The drawings and detailed description which follow are intended to be merely illustrative and are not intended to limit the scope of the invention as set forth in the appended claims.

FIG. 1 is a longitudinal view of a blood filter device according to one embodiment.

FIG. 2 is a longitudinal view of a blood filter device according to another embodiment, and in which the device is unsheathed and in an actuation position.

FIG. 3 is a longitudinal view of a blood filter device depicted in FIG. 2, and in which the device is unsheathed and in a release position.

FIG. 4 is a longitudinal view of a blood filter device according to another embodiment.

FIG. 5 is a cross-sectional view through section line 5-5 of the device depicted in FIG. 4, showing the connection between the balloon and mesh of the device.

FIG. 8 is a longitudinal view of a flexible arterial cannula showing standard features which are presently commercially available.

FIG. 11 is longitudinal view of a cannula with associated filter and distal flow diffuser.

FIG. 11a is a detail of the flow diffuser of FIG. 11.

FIG. 12 is a longitudinal view of a cannula with associated filter and distal flow diffuser.

FIG. 12a is a detail of the flow diffuser of FIG. 12.

DETAILED DESCRIPTION

Figure 6:
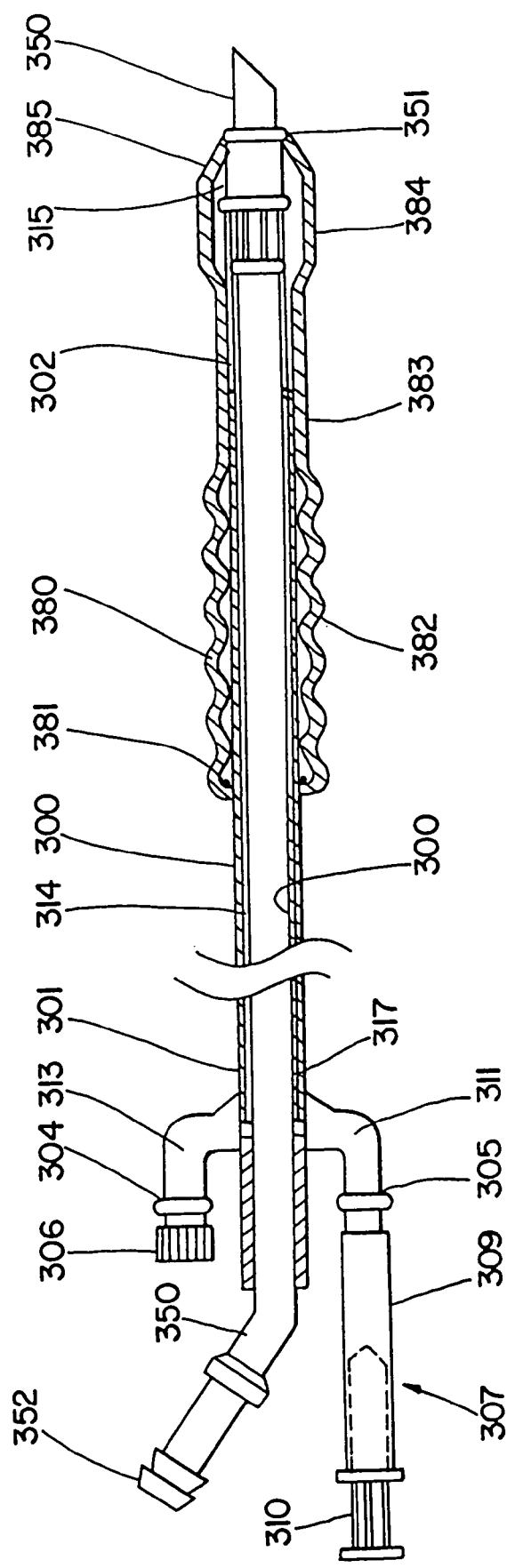
FIG. 6 is a longitudinal view of a blood filter device according to another embodiment, showing the filter contracted before deployment and contained under a retracting handle.

Referring more particularly to the drawings, FIG. 1 shows one embodiment of the blood filter device for use herein. The blood filter device 10 comprises an insertion tube 20, an umbrella frame 30, and an end plate 60, an activation tube 50, a mesh 40, an adjustment device 70, and a handle 80.

The device 10 is introduced into a vessel through a main port 7 of a cannula 5, and blood or other surgical equipment may be introduced into the main port 7 of the cannula 5 through a side port 3. The cannula 5 and the device 10 will not interfere with placement of equipment which may be used during a surgical procedure.

As shown in FIG. 1, the umbrella frame 30 comprises a plurality of arms 32 (some of which are not shown), which may include 3 arms, more preferably 4 arms, more preferably 5 arms, more preferably 6 arms, more preferably 7 arms, more preferably 8 arms, more preferably 9 arms, and most preferably 10 arms. The arms are sonically welded to a socket 34, which in turn is adhesive bonded to the insertion tube 20 which is dimensioned to fit within the main port 7 of the cannula 5 without unnecessarily impeding blood flow. Alternatively, the socket 34 may be connected to the insertion tube 20 by welding or epoxy. The insertion tube 20 is made of commercially available material such as polyvinyl, clear PVC, polyurethane, or other plastics. The arms 32 of the umbrella frame 30 are made of plastic or thin gage metal. Because of the flexibility of this material, the arms 32 bend without the need for extra parts such as hinges. This simplifies assembly and reduces the chances of misassembly. Each of the arms 32 is provided with an undercut to facilitate bending. Alternatively, the arms 32 may be made of a material having a shape memory characteristic, causing the arms to bend in the absence of external forces. A silicone material may be attached to the arms at the point at which they bend to act as a shock absorber. Alternatively, the arms may be coated with a hydrophilic coating or other shock absorbing material. Although the frame includes eight arms in one preferred embodiment, it is also contemplated that the umbrella frame may comprise more or less than eight arms.

The end plate 60 comprises a one-piece injection molded component, made of plastics or metal. The end plate 60 is substantially O-shaped with a radius r and indent in the center of the O-shape. The eight arms 32 of the umbrella frame 30 are sonic welded or bonded to the end plate 60 at eight arm junctures 61 spaced in 45 degree increments along a circumference of a circle defined by radius less than r. The activation tube 50 is welded or attached with epoxy to the indent 62.

The activation tube 50 extends from the end plate 60, through the insertion tube 20, to the adjustment device 70 housed in the handle 80 as shown in FIG. 1. The adjustment device 70 is a linear actuation device, comprising a thumb switch 72 which is attached to a guide frame 74 which in turn is attached to the activation tube 50 via a bond joint. Thumb switch 72 comprises a base 76 and a ratchet arm 78 which moves along a ratchet slot 82 along the top of the handle 80, locking in predetermined intervals in a manner known in the art. Sliding the thumb switch 72 away from the distal end 2 of the cannula 5 retracts the activation tube 50, which in turn draws the end plate 60 toward the handle 80. This causes the arms 32 of the umbrella frame 30 to bend and the mesh 40 to open and ready to trap foreign matter in the blood. Sliding thumb switch 72 toward the distal end 2 of the cannula 5 pushes the activation tube 50 in the direction of the mesh 40. The activation tube 50 then pushes the end plate 60 away from the handle 80, causing the arms 32 of the umbrella frame 30 to straighten and the mesh 40 to close.

If, in the alternative, the arms 32 of the umbrella frame 30 are made of a material with a shape memory characteristic, the linear actuation device must include a locking mechanism which, when locked, maintains the arms 32 in a straight position and which, when released, allows the arms 32 of the umbrella frame 30 to bend.

Other linear actuation devices known in the art also may be incorporated into the present invention such as, but not limited to, a friction fit slot device with a nub on the end, a device which incorporates hydraulic pressure or an electro-mechanical device with a motor.

To filter blood effectively, i.e., to entrap embolic material, without unduly disrupting blood flow, the mesh must have the appropriate physical characteristics, including area ($A_M$), thread diameter ($D_T$), and pore size ($S_P$). In the aorta, the mesh 40 must permit flow rates as high as 3 L/min or more, more preferably 3.5 L/min or more, more preferably 4 L/min or more, more preferably 4.5 L/min or more, more preferably 5 L/min or more preferably 5.5 L/min or more, and most preferably 6 L/min or more at pre-arterial pressures of around 120 mm Hg or less.

In order to entrap as many particles as possible, mesh with the appropriate pore size must be chosen. The dimensions of the particles to be entrapped are an important factor in this choice. In the aorta, for example, particle size has been found to range from 0.27 to 2.88 mm. with a mean of 0.85 mm, and particle volume has been found to range from 0.01 to 12.45 mm$^3$, with a mean of 0.32 mm$^3$. Approximately 27 percent of the particles have been found to measure 0.6 mm or less in diameter. During cardiac bypass surgery in particular, aortic embolic load has been found to range from 0.57 cc to 11.2 cc, with a mean of 3.7 cc, and an estimated cerebral embolic load has been found to range from 60 to 510 mm$^3$, with a mean of 276 mm$^3$.

When a bubble greater than 100 μm diameter encounters the filter, there must be sufficient pressure on the proximal side of the filter to force the bubble through the pore. The surface tension of the blood generally prevents the bubble from deforming and extruding through the pore, but rather the bubble breaks apart into a plurality of bubbles small enough to pass freely through the pore. The filter thereby acts as a bubble sieve.

The benefit of reducing the size of the interactive bubbles is twofold. First, the potential of a bubble to cause ischemia is directly related to its diameter. The larger the bubble, the more likely it is to block blood flow to a larger area of the brain. Smaller bubbles may block smaller arteries, but will have less overall ischemic effect. Second, smaller bubbles will be absorbed into tissue and cells more quickly than large bubbles, because of their greater surface area to volume ratio. The net effect is smaller bubbles which may make their way into the brain, and bubbles which will be more quickly metabolized further reducing risk of embolic ischemia.

Another method by which large bubbles can be rendered into smaller bubbles is due to velocity and momentum effects. During moments of peak systolic cardiac output, the blood velocity from the heart is at its maximum (100-150 cm/s). If a bubble is trapped against the intra-aortic filter and is subject to instantaneous high velocity blood flow, the momentum of the blood on the bubble will cause the bubble to shatter into smaller bubbles. The smaller bubbles will then "escape" through the pores in the filter if they have been rendered small enough.

By way of example, when a device of the present invention is intended for use in the aorta, the area of the mesh required for the device 10 is calculated in the following manner. First, the number of pores $N_P$ in the mesh is calculated as a function of thread diameter, pore size, flow rate, upstream pressure and downstream pressure. This is done using Bernoulli's equation for flow in a tube with an obstruction:

$$\frac{P_1}{\rho * g} + \frac{V_1^2}{2*g} = \frac{P_2}{\rho * g} + \frac{V_2^2}{2*g} * A$$

In this equation, P is pressure, $\rho$ is density of the fluid, g is the gravity constant (9.8 m/s$^2$), V is velocity, K represents the loss constants, and f is the friction factor. The numbers 1 and 2 denote conditions upstream and downstream, respectively, of the filter.

The following values are chosen to simulate conditions within the aorta:
 $P_1$=120 mm Hg;
 $P_2$=80 mm Hg;
 $K_{entry}$=0.5;
 $K_{exit}$=1.0;
 K=$K_{entry}$+$K_{exit}$; and $$\left[\frac{D_T}{S_P}\right]_{Equiv}$$

is 30.

Assuming laminar flow out of the mesh filter, f is given as $$\frac{64}{Re}$$

where Re is the Reynold's number and the Reynold's number is given by the following equation:

$$Re = \frac{(\rho * Q * S_P)}{(\mu * N_P * A_h)}$$

where $\mu$ is the kinematic viscosity of the fluid and $A_h$ is the area of one hole in the mesh given by $S_P * S_P$.

Conservation of the volume dictates the following equation:

$$N_P * V_2 * A_h = Q \text{ OR } V_2 = \frac{Q}{(N_P * A_h)}$$

where Q is the flow rate of the blood. In addition, $V_1$ is given by:

$$V_1 = \frac{Q}{A_{vessel}}$$

where $A_{vessel}$ is the cross-sectional area of the vessel. Substitution and manipulation of the above equations yields $N_P$.

Next, the area of the mesh is calculated as a function of the number of pores, thread diameter and pore size using the following equation:

$$A_M = N_P * (D_T + S_P)^2$$

In an embodiment of the device 10 that is to be used in the aorta, mesh with dimensions within the following ranges is desirable: mesh area is 3-10 in$^2$, more preferably 4-9 in$^2$, more preferably 5-8 in$^2$, more preferably 6-8 in$^2$, most preferably 7-8 in$^2$; mesh thickness is 20-280 μm, more preferably 23-240 μm, more preferably 26-200 μm, more preferably 29-160 μm, more preferably 32-120 μm, more preferably 36-90 μm, more preferably 40-60 μm; thread diameter is 10-145 μm, more preferably 12-125 μm, more preferably 14-105 μm, more preferably 16-85 μm, more preferably 20-40 μm; and pore size is 50-300 μm, more preferably 57-285 μm, more preferably 64-270 μm, more preferably 71-255 μm, more preferably 78-240 μm, more preferably 85-225 μm, more preferably 92-210 μm, more preferably 99-195 μm, more preferably 106-180 μm, more preferably 103-165 μm, more preferably 120-150 μm. In a preferred embodiment of the invention, mesh area is 3-8 in$^2$, mesh thickness is 36-90 μm, thread diameter is 16-85 μm, and pore size is 103-165 μm. In a further preferred embodiment of the invention, mesh area is 3-5 in$^2$, mesh thickness is 40-60 μm, thread diameter is 20-40 μm, and pore size is 120-150 μm.

The calculation set forth above has been made with reference to the aorta. It will be understood, however, that blood flow parameters within any vessel other than the aorta may be inserted into the equations set forth above to calculate the mesh area required for a blood filter device adapted for that vessel.

To test the mesh under conditions simulating the conditions within the body, fluid flow may be observed from a reservoir through a pipe attached to the bottom of the reservoir with the mesh placed over the mouth of the pipe through which the fluid exits the pipe. A mixture of glycerin and water may be used to simulate blood. Fluid height (h) is the length of the pipe in addition to the depth of the fluid in the reservoir, and it is given by the following equation:

$$h = \frac{P}{(\rho * g)}$$

where ρ is given by the density of the glycerin-water mixture, and g is given by the gravity constant (9.8 ms²).

Bernoulli's equation (as set forth above) may be solved in order to determine $(D_T/S_P)_{Equiv}$. $V_1$ is given by the following equation:

$$V_1 = \frac{Q}{A_1}$$

where Q is the flow rate which would be measured during testing and $A_1$ is the cross-sectional area of the pipe. $V_2$ is given by the following equation:

$$V_2 = \frac{Q}{(N*A_2)}$$

$$Re = \frac{(\rho * V_2 * D)}{\mu}$$

where N is the number of pores in the mesh and $A_2$ is the area of one pore. Further, $P_1$=120 mm Hg and $P_2$=0 mm Hg and $S_P$ is the diagonal length of the pore. Reynold's number (Re) is given by the following equation:

where ρ and μ are, respectively, the density and kinematic viscosity of the glycerin-water mixture.

Once appropriate physical characteristics are determined, suitable mesh can be found among standard meshes known in the art. For example, polyurethane meshes may be used, such as Saati and Tetko meshes. These are available in sheet form and can be easily cut and formed into a desired shape. In a preferred embodiment, the mesh is sonic welded into a cone shape. Other meshes known in the art, which have the desired physical characteristics, are also suitable. The mesh 40 is sonic welded or adhesive bonded to the arms 32 of he umbrella frame 30 from the end plate 60 to a point on each arm 32 between the end plate 60 and the socket 34 as shown in FIG. 1. This is the optimal placement of the Mesh 40 when the device 10 is inserted into the vessel in the direction of the blood flow. However, it is also contemplated that the device 10 may be inserted in a direction opposite the blood flow. In this case, the mesh 40 would be attached to the arms 32 of the umbrella frame 30 from the socket 34 to a point on each arm 32 between the socket 34 and the end plate 60.

Anticoagulants, such as heparin and heparinoids, may be applied to the mesh 40 to reduce the chances of blood clotting on the mesh 40. Anticoagulants other than heparinoids also may be used. The anticoagulant may be painted or sprayed onto the mesh. A chemical dip comprising the anticoagulant also may be used. Other methods known in the art for applying chemicals to mesh may be used.

The device 10 may be used in the following manner. A cannula 5 is introduced into the vessel through an incision made in the vessel wall, and the cannula 5 is then sutured to the vessel wall. The cannula 5 is preferably size 22-25 French (outer diameter). The blood filter device 10 is then inserted into the vessel through the cannula 5. Within the cannula 5, the blood filter device 10 is maintained in a release position in which the arms 32 of the umbrella frame 30 are straight and the mesh 40 is closed. (See FIG. 3.)

In order to actuate the device 10, the surgeon slides the thumb switch 72 of the adjustment device 70 along the ratchet slot 82, away from the distal end 2 of the cannula 5, until an appropriate actuation position is achieved or until the mesh 40 is opened to its maximum size. (See FIG. 2.) The arms 32 may bend to varying degrees in a plurality of actuation positions, and the appropriate actuation position depends on the cross-sectional dimension of the blood vessel. During filtration, a user may gently palpate the outside of the blood vessel to feel points of contact between the vessel wall and the device 10. This enables the user to determine the appropriate actuation position and the location of the device within the vessel.

When filtration has been completed, the user slides the thumb switch 72 toward the distal end 2 of the cannula 5, thereby effecting the release position, in which the arms 32 of the umbrella frame 30 straighten and the mesh 40 closes around the captured emboli. (See FIG. 3.)

The handle 80 may be additionally provided with a marker band which matches up with a corresponding marker band on the thumb switch 72 when the device 10 is in the release position. The device 10 is pulled back into the cannula 5, and then cannula 5 and the device 10, along with the captured emboli, are removed from the body.

In another embodiment, a blood filter device is provided as illustrated in FIGS. 2 and 3. The device 10 comprises an introducer 103, a cannula 105, having a distal end 111, a sheath 120, an umbrella frame 130, an annular mesh 140, a movable ring 150, a fixed ring 160, guidewires 170, and a clam-shell handle 180.

The introducer 103 comprises a cylinder 107 and an adjustable suture ring 109. The cylinder 107 of the introducer 103 is made to fit around the sheath 120, which slides over the cannula 105 and the guidewires 170.

The umbrella frame 130 is substantially similar to the umbrella frame 30 depicted in FIG. 1. The umbrella frame 130 comprises a plurality of arms 132 (some of which are not shown) as discussed above with reference to FIG. 1, which arms are connected at one end (of each arm 132) to the fixed ring 160 and at the other end (of each arm 132) to the movable ring 150. The fixed ring 160 is firmly secured to the cannula 105. Each guidewire 170 is firmly secured at one end to the movable ring 150m, which slides along the outer surface of the cannula 105, and at the other end to the clamshell handle 180, which is a linear actuation device known in the art.

The mesh 140 must entrap embolic material without unduly disrupting blood flow. This mesh 140 also may be found among standard meshes known in the art. The same analysis used to select and test the mesh 40 of the first preferred embodiment may be used to select the mesh 140.

The device 10 is used in the following manner. The device 10 is inserted into the blood vessel. The sheath 120 is retracted until it exposes the umbrella frame 130. A user effects the actuation position by pushing the movable ring 150 toward the fixed ring 160 via the clam-shell handle 180 and the guidewires 170 as shown in FIG. 2. In the actuation position, the arms 132 of the umbrella frame 130 are bent and the annular mesh 140 is open and ready to capture foreign matter in the blood.

In order to remove the blood filter 10 from the body, the user first pulls the movable ring 150 away from the fixed ring 160 via the clamshell handle 180 and the guidewires 170. This causes the arms 132 of the umbrella frame 130 to straighten and the annular mesh 140 to close, trapping the emboli against the cannula 105. The user then removes the blood filter device 10 from the body along with the captured emboli. Alternatively, the user may first slide the sheath 120 back over the cannula 105, and then remove the device 10 from the body along with the captured emboli.

In an alternative embodiment adapted for use in the aorta during cardiac surgery, a second mesh may be placed over the distal end 111 of the cannula 105 or within the cannula 105 so that blood flowing into the body from an extracorporeal source is also filtered. Alternatively, in lieu of an annular mesh 140 and a second mesh, a single mesh may be used which is configured such that it covers the distal end 111 of the cannula 105.

An advantage of the embodiment depicted in FIG. 2 is that it does not require a cannula with a separate port for the introduction of blood or a surgical equipment.

FIG. 4 shows another embodiment of the blood filter device disclosed herein. As shown in FIG. 4, the blood filter device 10 comprises a mesh 220, an inflatable balloon 230, a collar 240, a plurality of tie lines 250, and an actuation assembly 260. The mesh 220 is attached to the balloon 230 via the collar 240. In use, the device 10 is positioned and maintained in a blood vessel via the plurality of tie lines 250. Manipulation of actuation assembly 260 inflates and deflates the balloon 230 and controls the degree of inflation and deflation. Inflation of the balloon 230 opens the mesh 220, and deflation of the balloon 230 allows the mesh 220 to close.

Mesh 220, found among standard meshes as in the first two embodiments, should cover substantially all of the cross-sectional area of a vessel so that blood flowing in the vessel must pass through the mesh 220. In this way, foreign matter in blood within the vessel is entrapped by the mesh 220. In the preferred embodiment, the mesh 220 is generally cone-shaped. However, the shape of the mesh 220 may be modified to assume any shape as long as blood flowing in the vessel passes through the mesh 220.

As shown in FIG. 4, inflatable balloon 230 is attached to the mesh 220 via the collar 240. In a preferred embodiment, the balloon 230 is made of two pieces of a flexible, slightly porous material such as urethane or polyethylene terephalate (PET), each piece having an outer diameter and an inner diameter. These pieces are welded together at both the outer and inner diameters in a manner known in the art. The balloon 230 also has a valve 268 and a valve stem 266 located between the outer diameter and the inner diameter of the balloon 230. Material used for the balloon 230 must be capable of inflation and deflation. It also must be sufficiently flexible to conform to the walls of a vessel regardless of possible irregularities in the walls, such as may be caused by plaque or other materials adhering to the walls. Material used for the balloon 230 also must be sufficiently flexible to allow the balloon 230 to fold up within a cannula 205. Exemplary materials include elastomeric and certain non-elastomeric balloons.

To inflate the balloon 230 and thereby open the mesh 220, a fluid or a gas, is introduced into the balloon 230 through the valve 268. To deflate the balloon 230, the fluid or gas is removed from the balloon 230 through the valve 268. Fluids such as saline may be used, and gases such as inert gases may be used with this invention. Any fluid or gas may be used as long as it does not harm the patient if released into the bloodstream. The saline or other suitable inflation material is typically stored in a reservoir outside the body, which is capable of fluid communication with the balloon 230 through a tube 264.

In an embodiment of the devices suited for placement in the aorta, the balloon 230 has an outer diameter of approximately 100 Fr., more preferably 105 Fr., more preferably 110 Fr., more preferably 115 Fr., more preferably 120 Fr., and most preferably 125 Fr., or greater, and an inner diameter of approximately 45 Fr. (1 Fr.=0.13 in.) when fully inflated. The dimensions of the balloon 230 may be adjusted in alternative embodiments adapted for use in vessels other than the aorta. Alternatively, expandable members other than a balloon also may be used with this invention.

Referring to FIG. 4, the collar 240 is attached to the outer diameter of the balloon 230 and is a generally circular piece of plastic. Other materials, such as silicone or high density polyethylene may be used. This material should be rigid enough to withstand flow conditions in blood vessels, yet flexible enough to expand as the balloon 230 is inflated and to fold up as the balloon 230 is deflated and stored within the cannula 205. The collar 240 has both an inner and outer diameter, and the outer diameter is bent slightly outward. As shown in FIG. 5, the collar 240 is attached to the outer diameter of the balloon 230 by welding, adhesive or other attachment means known in the art. The mesh 220, in turn, is adhesive bonded to the collar 240. Alternatively, the mesh 220 may be connected to the collar 240 by welding, epoxy, or other suitable adhesive means.

Actuation of the device 10 is accomplished by the actuation assembly 260, which inflates and deflates the balloon 230 by introducing into and removing from the balloon 230 the fluid or gas. The actuation assembly 260 also controls the degree to which the mesh is opened within the blood vessel. The actuation assembly 260 may be used to adjust the fit of the device 10 within the vessel during filtration or use of the device 10. In addition, because the degree to which the mesh is opened may be adjusted by the actuation assembly 260, one embodiment of the device may be suitable for a variety of vessel sizes.

Actuation assembly 260 comprises an inflation catheter 262 and the tube 264 which is connected to the valve stem 266. The inflation catheter 262 is preferably 9 F.O.D. and is marked in cubic centimeter increments in order to monitor the degree to which the balloon 230 is inflated. The tube 264 is preferably size 12 Fr.O.D. and 7.2 Fr.I.D.

A plurality of tie lines 250, which may include three tie lines, four tie lines, or more than four tie lines, position and maintain the device 10 in place in the bloodstream. The tie lines 250 are made of wire and are threaded through the balloon 230 at points equally spaced along the inner diameter of the balloon, e.g., for four tie lines the four points are space 90 degrees apart along the inner diameter of the balloon 230. The tie lines 250 may be made of other materials having sufficient stiffness to push and pull the balloon 230 out of and into the cannula 205 and to maintain the device 10 within the blood vessel.

All components of this device should be composed of materials suitable for insertion into the body. Additionally, sizes of all components are determined by dimensional parameters of the vessels in which the devices are intended to be used. These parameters are known by those skilled in the art.

By way of purely illustrative example, the operational characteristics of a filter according to the invention and adapted for use in the aorta are as follows:

| | |
|---|---|
| Temperature Range | 25-39 degrees C. |
| Pressure Range | 50-120 mm Hg |
| Flow Rate | usually up to 5 L/min., can be as high as 6 L/min. |
| Duration of single use | up to approximately 5 hours |
| Average emboli trapped | 5-10,000 |
| Pressure gradient range | (100-140)/(50-90) |

Modification of the operational characteristics set forth above for use of the present invention in vessels other than the aorta are readily ascertainable by those skilled in the art in view of the present disclosure.

An advantage of all embodiments disclosed herein is that the blood filter will capture emboli which may result from the incision through which the blood filter is inserted.

In use, there are a number of methods for protecting patients from embolization and for filtering blood using the devices disclosed herein. Temporary filtration is frequently required in association with procedures performed on blood vessels because there is a possibility of embolization associated with such procedures. For example, there is a correlation between embolization and the aortic clamping and unclamping which is performed during cardiac bypass surgery.

The devices of the present invention are particularly suited for use in methods of the present invention. However, other devices may be adapted for use in accordance with the methods of the present invention.

The methods of the present invention generally include the following steps: introducing a blood filter device into a blood vessel of a patient to entrap embolic matter or foreign matter in the blood; and removing the mesh and the entrapped foreign matter from the blood vessel. The blood filter device also may be adjusted if this is necessary during the course of filtration.

In addition, use of visualization techniques is also contemplated in order to determine which patients require filtration (identify risk factors), where to effectively position a blood filter device to maximize effectiveness, when to adjust the device if adjustment is necessary, when to actuate the device and appropriate regions for performing any procedures required on a patient's blood vessel.

According to one method of the present invention, the blood filter device depicted in FIGS. 4 and 5 is introduced into a patient's blood vessel. Typically, an incision is first made in a vessel of a patient, and, with reference to FIG. 4, cannula 205 is introduced into the incision in the direction of blood flow. Within the cannula 205, the device 10 is stored in a closed position in which the balloon is deflated and generally folded in upon itself and the mesh 220 is closed.

The blood filter device 10 is then pushed out through the cannula 205 into the vessel by pushing the tie lines 250 in the direction of blood flow. To actuate the device 10, the actuation assembly 260 inflates the balloon until the balloon 230 opens the mesh 220 within the vessel to cover substantially all of the cross-sectional area of the vessel such that blood flowing through the vessel flows through the mesh 220. As the blood flows through the mesh 220, foreign matter is entrapped by the mesh.

When the filter is no longer needed, the device 10 is removed from the vessel along with the entrapped foreign matter. The balloon 230 is deflated, and the tie lines 250 are pulled toward the cannula opposite the direction of the blood flow. As the balloon 230 is pulled into the cannula 205, the balloon 230 folds in upon itself, and the mesh 220 closes around the entrapped foreign matter. In an alternative embodiment, the cannula 205 may be configured to further accommodate entry of the balloon 230, the mesh 220, and the entrapped foreign matter into the cannula 205 without disturbing blood flow. For example, the end of the cannula placed within the vessel may be very slightly flared.

In accordance with one aspect of the invention, a visualization technique, such as TCD, is used to determine when to actuate a blood filter device. For example, during cardiac bypass surgery, flurries of emboli are detected during aortic cannulation, inception, and termination of bypass and cross-clamping of the aorta. Therefore, a mesh may be opened within a vessel downstream of the aorta during these procedures and closed when embolization resulting from these procedures has ceased. Closing the mesh when filtration is not required helps to minimize obstruction of the blood flow.

According to another embodiment, a visualization technique is used to monitor emboli entering cerebral circulation to evaluate the effectiveness of a blood filter device in trapping emboli. Also, a visualization technique is useful to positioning a device within a vessel so that it operates at optimum efficiency. For example, a user may adjust the position of the device if TCD monitoring indicates emboli are freely entering the cerebral circulation. In addition, a user may adjust a mesh of a blood filter device to ensure that substantially all of the blood flowing in the vessel passes through the mesh.

According to yet another embodiment, a visualization technique, such as TEE and epicardial aortic ultrasonography, is used to identify those patients requiring blood filtration according to the present invention. For example, these visualization techniques may be used to identify patients who are likely to experience embolization due to the presence of mobile plaque. These techniques may be used before the patient undergoes any type of procedure which will affect a blood vessel in which mobile plaque is located.

Additionally, visualization techniques may be used to select appropriate sites on a blood vessel to perform certain procedures to eliminate or reduce the occurrence of embolization. For example, during cardiac bypass surgery, the aorta is both clamped and cannulated. These procedures frequently dislodge atheromatous material already present on the walls of the aorta. To minimize the amount of atheromatous material dislodged, a user may clamp or cannulate a section of the aorta which contains the least amount of atheromatous material, as identified by TEE, epicardial aortic ultrasonography or other visualization technique.

Procedures other than incising and clamping also tend to dislodge atheromatous material from the walls of vessels. These procedures include, but are not limited to, dilatation, angioplasty, and atherectomy.

Visualization techniques also may be used to select appropriate sites for filtering blood. Once atheromatous material is located within a vessel, a blood filter device may be placed downstream of that location.

Visualization techniques, other than those already mentioned, as are known to those skilled in the art, are also useful in ascertaining the contours of a blood vessel affected by surgical procedure to assess a variety of risk of embolization factors, and to locate appropriate sections of a vessel for performing certain procedures. Any suitable visualization device may be used to evaluate the efficacy of a device, such as those disclosed herein, in trapping emboli.

Figure 7:
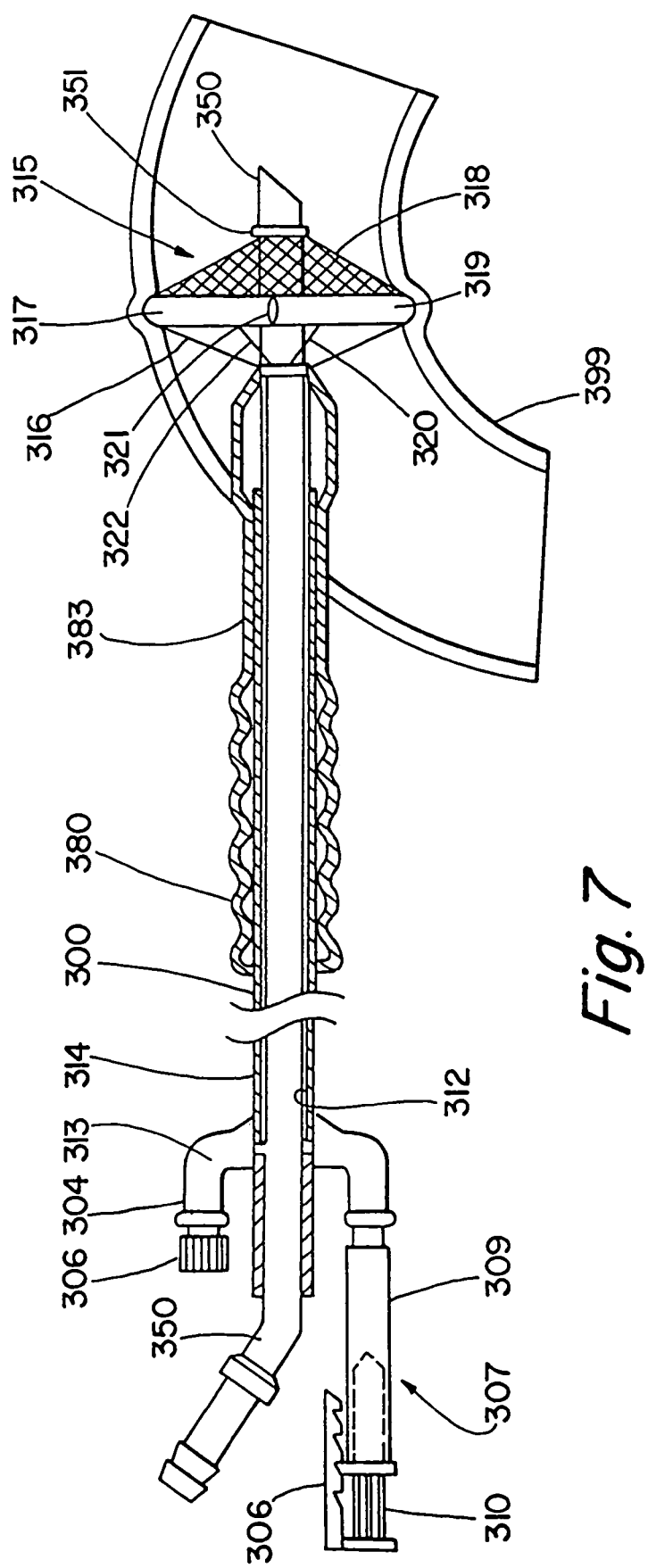
FIG. 7 is a longitudinal view of the blood filter device depicted in FIG. 6, showing the filter deployed after insertion of the cannula into the aorta.

In another embodiment, a cannula with associated filter is provided as depicted in FIGS. 6 and 7. With reference to FIG. 6, the device includes a pressurizing cannula 300 having proximal region 301, distal region 302, and an intermediate region which connects the proximal and distal regions. The pressurizing cannula 300 is typically a rigid or semi-rigid, preferably transparent tube having a first substantially cylindrical lumen 303 which extends from the proximal region to the distal region and is shaped to receive blood supply cannula 350. The pressurizing cannula 300 further includes at its proximal region luer fittings 304 and 305 which are shaped to receive a cap or septum 306 and a syringe 307 filled with saline or gas and having a locking mechanism 308 (FIG. 7) for locking the barrel 309 and plunger 310 in a fixed position. The pressurizing cannula 300 typically has a dual lumen to effect pressurization of the inflation seal (discussed below). Thus luer 305 is connected to passage 311 which is in fluid communication with a second lumen 312 which extends from the proximal to the distal end of pressurizing cannula 300. Meanwhile, luer 304 is connected to passage 313 which is in fluid communication with a third lumen 314 which extends from the proximal to the distal end of pressurizing cannula 300. At its distal region, the pressurizing cannula 300 includes a blood filtration assembly 315 which is shown in greater detail in FIG. 7.

FIG. 8 depicts a standard flexible arterial cannula 400 which is commercially available from Sarns 3M (Ann Arbor, Mich.). With reference to FIG. 8, the cannula will typically have a length of about 25 cm. The cannula includes a distal end region 401, a proximal end region 402, and an intermediate region disposed therebetween. Distal end region 401 has an outer diameter of about 8 mm, and a sealing ring 403 having an enlarged diameter of about 13 mm, a width of about 5 mm, and being disposed about 25 mm from the distal tip of cannula 400. Sealing ring 403 functions as an anchor point against the inside of an aortic incision so that cannula 400 does not slide from the aorta during a procedure. Proximal end region 402 includes a connector 404 which joins the cannula to the blood machine. At its proximal tip, the cannula includes a tapered joint 405 which connects and locks the cannula to a bypass-oxygenator machine.

Referring again to FIG. 6, blood supply cannula 350 may have certain features in common with the standard cannula 400 depicted in FIG. 8. Blood supply cannula 350 for use herein is a substantially cylindrical, semi-rigid, and preferably transparent tube which includes a rib 351 disposed about the circumference at a distal region thereof. The blood cannula is slideable within the pressurizing cannula, and in the proximal region, the blood cannula 350 may be angled to adopt a shape which does not interfere with syringe 307. Moreover, the blood cannula will typically include a fitting or molded joint 352 which is adapted for coupling to a bypass-oxygenator system. Blood cannula 350 is adapted to carry blood to the aorta from the bypass-oxygenator system.

The pressurizing cannula may also include an inserting and retracting handle 380 comprising a substantially cylindrical tube disposed about the intermediate region of pressurizing cannula 300. Handle 380 will generally include a rigid or semi-rigid, preferably transparent tube with molded hand grip to facilitate holding and inserting. With reference to FIG. 7, handle 380 is slideable relative to the pressurizing cannula 300, and may include a sealing member 381 comprising a rubber washer or O-ring mounted in a proximal region of the handle and disposed between handle 380 and pressurizing cannula 300 to prevent leakage of blood therebetween. Handle 380 may include corrugation ribs 382 and its proximal and intermediate regions, and a substantially flat or level collar insertion region 383 adapted to fit tightly against vessel material at an aortic incision. In certain embodiments, the collar insertion region 383 will include a sealing ring or rib (not shown), having a width of about 5 mm and an outer diameter of about 13 mm, which serves as an anchor against the aorta to prevent the cannula assembly from slipping out during a surgical procedure. A "purse string" suture is generally tied around the circumference of the aortic incision, and this string will be tightened around the ring in collar region 383 to prevent slippage of the cannula assembly.

Handle 380 may also include an enlarged end region 384 which encloses the blood filtration assembly 315 as depicted before insertion in FIG. 6. This housing enclosure 384 is a particularly preferred component because it prevents inadvertent deployment of the blood filtration assembly, and it provides a smooth outer surface to the cannula which facilitates entry through an incision in the aorta without tearing the aorta. In the absence of such housing enclosure, the balloon and filter are liable to scrape against the inner wall of a vessel, and thereby damage or rupture the vessel. At its distal end, handle 380 may include inverted cuff 385 which bears against rib 351 of blood cannula 350 to form a seal when the filtration assembly 315 is enclosed in handle 380.

With reference to FIG. 7, the distal region of pressurizing cannula 300 is shown with blood filtration assembly 315 deployed in the ascending region of a human aorta 399. Handle 380 has been moved proximally to expose filter assembly 315. The distal region of pressurizing cannula 300 includes a plurality of spokes or holding strings 316 made from Dacron™ or other suitable material. Holding strings 316 connect the distal region of the pressurizing cannula 300 to an inflation seal 317 which comprises a continuous ring of preferably thin tubing attached to filter mesh 318 on its outer side. Filter mesh 318 is bonded at its distal end around the circumference of blood cannula 350, preferably at a cross-sectional position which closely abuts rib 351.

Inflation seal 317 may be constructed from elastomeric or non-elastomeric tubular material which encloses donut-shaped chamber 319. When deployed, the inflation seal will expand to a diameter which fits tightly against the lumen of aorta 399. The inflation seal will thus be capable of expansion to an outer diameter of at least 2 cm, more preferably at least 2.5 cm, more preferably at least 3 cm, more preferably at least 3.5 cm, more preferably at least 4 cm, more preferably at least 4.5 cm. These diameter ranges will accommodate both pediatric use and adult use. The inflation seal is typically a continuous ring of very thin tubing attached to the mesh filter on one side and to the pressurizing cannula by holding strings on the other side.

The inflation seal should be able to maintain an internal pressure in chamber 319, without bursting, of greater than 55 mm Hg, more preferably greater than 60 mm Hg, more preferably greater than 70 mm Hg, more preferably greater than 80 mm Hg, more preferably greater than 90 mm Hg, more preferably greater than 100 mm Hg, more preferably greater than 110 mm Hg, more preferably greater than 120 mm Hg, more preferably greater than 130 mm Hg, more preferably greater than 140 mm Hg, more preferably greater than 150 mm Hg. The internal pressure needed will depend on the pressure maintained in the aorta against the mesh. Thus, if the aortic pressure is 55 mm Hg, then the pressure in the inflation seal must be greater than 55 mm Hg to prevent leakage around the seal. Typically, the aortic pressure will be at least 75 mm Hg because this level of pressure is needed to ensure adequate brain perfusion. It will be recognized that such inflation seal pressures are much higher than the maximum level that can be used in the pulmonary venous system because the veins and arteries therein will typically hold no more than about 40-50 mm Hg, or at most 60 mm Hg without rupture.

Chamber 319 is in fluid communication with a first tubular passage 320 and a second tubular passage 321 which permit chamber 319 to be inflated with gas, or preferably a fluid such as saline. Passage 320 is in fluid communication with second lumen 312 of pressurizing cannula 300, while passage 321 is in fluid communication with third lumen 314 of pressurizing cannula 300. Passage 320 and 321 thereby interconnect chamber 319 with the second and third lumens 312 and 314, respectively, of pressurizing cannula 300.

In certain embodiments, inflation seal 317 will include a septum 322 which blocks the movement of fluid in one direction around chamber 319. If septum 322 is positioned in close proximity to the fluid entry port, then the injection of fluid will push all gas in chamber 319 around inflation seal 317 and out through passage 321. In one embodiment, the entry port and the exit port are positioned in close proximity with septum 322 disposed between the entry and exit port. In this case, injection of fluid will force virtually all gas out of inflation seal 317.

Filter mesh 318 is bonded at its proximal end to inflation seal 317 and at its distal end to blood cannula 350, optionally at the proximal or distal edge of rib 351. Mesh 318 can be made of a material which is reinforced or non-reinforced. Mesh 318, when expanded as shown in FIG. 7, may assume a substantially conical shape with a truncated distal region. The mesh should be formed of a material having a pore size which obstructs objects 5 mm in size or less, more preferably 3 mm in size, more preferably less than 3 mm, more preferably less than 2.75 mm, more preferably less than 2.5 mm, more preferably less than 2.25 mm, more preferably less than 2 mm, more preferably less than 1.5 mm, more preferably less than 1 mm, more preferably less than 0.75 mm, more preferably less than 0.5 mm, more preferably less than 0.25 mm, more preferably less than 0.1 mm, more preferably less than 0.075 mm, more preferably less than 0.05 mm, more preferably less than 0.025 mm, more preferably 0.02 mm, and down to sizes just larger than a red blood cell. It will be understood that for a given pore size that blocks particles of a certain size as stated above, that pore size will block all particles larger than that size as well. It should also be understood that the necessary pore size is a function of blood throughput, surface area of the mesh, and the pressure on the proximal and distal side of the mesh. For example, if a throughput of 5-6 L/min. is desired at a cross-section of the aorta having a diameter of 40 mm, and a pressure of 120 mm Hg will be applied to the proximal side of the mesh to obtain a distal pressure of 80 mm Hg, then a pore size of about □50 □m is needed. By contrast, in the pulmonary artery the same throughput is needed, but the artery cross-section has a diameter of only 30 mm. Moreover, the proximal pressure is typically 40-60 mm Hg, while the distal pressure is about 20 mm Hg. Thus, a much larger pore size is needed to maintain blood flow. If pore sizes as disclosed herein for the aorta were used in the pulmonary artery, the blood throughput would be insufficient to maintain blood oxygenation, and the patient would suffer right ventricular overload because of pulmonary artery hypertension.

It will also be understood for this cannula apparatus that blood flow to the patient is maintained by blood passage through blood cannula 350, and not through mesh 318. Thus, the cannula must have an inner diameter which allows blood throughput at a mean flow rate of at least 3.0 L/min., more preferably 3.5 L/min., more preferably 4 L/min., more preferably at least 4.5 L/min., more preferably at least 5 L/min., and more. Of course, flow rate can vary intermittently down to as low as 0.5 L/min. Therefore, the inner diameter of blood supply cannula 350 will typically be at least 9 F (3.0 mm), more preferably 10 F, more preferably 11 F, more preferably 12 F (4 mm), more preferably 13 F, more preferably 14 F, more preferably 15 F (5 mm), and greater. Depending on the inner diameter and thickness of the tubing, the outer diameter of blood cannula 350 is approximately 8 mm. Meanwhile, the pressurizing cannula 300 and handle at the collar region 383 have outer diameters of approximately 10.5 mm and 13.0 mm, respectively. The foregoing ranges are intended only to illustrate typical device parameters and dimensions, and the actual parameters may obviously vary outside the stated ranges and numbers without departing from the basic principles disclosed herein.

In use, the cannula with associated filter has syringe 307 which is removed, and aseptically filled with a saline solution. The syringe is then attached to pressurizing cannula 300, and cap 306 is removed. Saline is injected until saline exits from luer 304, thereby purging substantially all gas from the inflation seal and dual lumen system of pressurizing cannula 300. Cap 306 is then replaced and secured to the pressurizing cannula 300.

Cardiac surgery can then be conducted in accordance with procedures which employ standard cannula insertion, as known in the art, and discussed more fully herein. The mesh 318 and inflation seal 317 are enclosed under handle 380 at the enlarged end, just beyond the distal tip of pressurizing cannula 300. The cannula is introduced into the aorta, preferably the ascending aorta, of a patient through an incision, and the incision may be tightened about the cannula by use of a "purse string" suture. Cardiopulmonary bypass occurs through blood cannula 350.

With the cannula in place, the filter is ready for deployment. The surgeon grips the handle, and the blood cannula 350 and pressurizing cannula 300 are pushed forward. This movement breaks the seal at the tip of the handle and allows the blood cannula and pressurizing cannula to thrust forward, thereby releasing the filter. The plunger of the syringe is then depressed within the barrel to expand the inflation seal. The inflation seal expands to ensure contact with the inside of the aorta at all points along the circumference of the lumen. The syringe is then locked in place to prevent inflation or depressurization of the inflation seal during use.

The aorta is then cross-lamped at a region between the heart and the cannula incision. Embolic material dislodged from the aorta is caught and trapped by filter mesh 318. The bypass-oxygenator system is then started to achieve cardiopulmonary bypass through blood cannula 350. Cardiac surgery is then performed while the filter and inflation seal are maintained in place for a number of hours, typically 8 hours or less, more typically 7 hours or less, more typically 6 hours or less, more typically 5 hours or less, more typically 4 hours or less, more typically 3 hours or less, and more typically 2 hours or less.

At the end of the cardiac surgery, the filter is depressurized and removed from the ascending aorta. The syringe lock is released and, while holding handle 380, the pressurizing cannula is drawn back. This will cause release of saline from inflation seal 317, and will retrieve the filter mesh, inflation seal, and pressurizing cannula back into and under the handle, as it was configured before deployment. Notably, embolic material collected in the filter is also trapped under the handle at its enlarged segment. Optionally, the inflation seal may be deflated before pull-back of the pressurizing cannula by operating the syringe to withdraw saline from the inflation seal. Once the associated filter has been retrieved under the handle, the cannula can be removed from the patient without damaging the aortic incision by using standard procedures.

Figure 9:
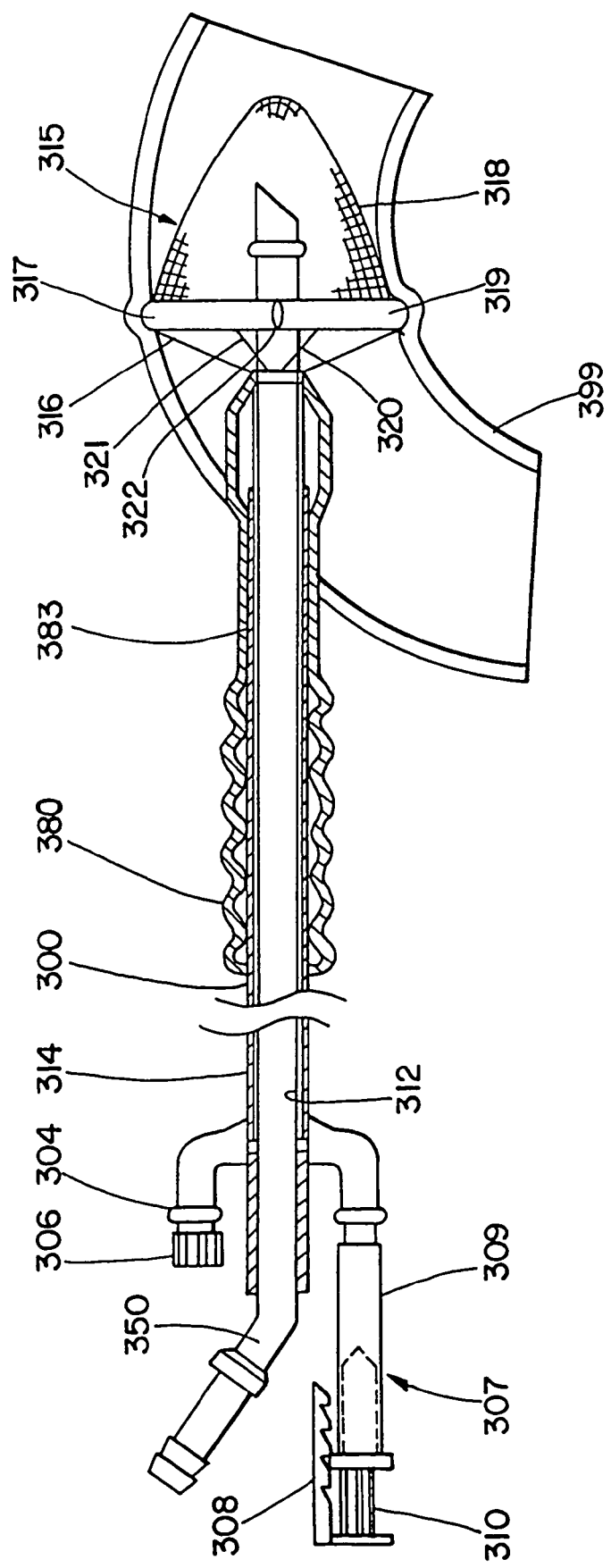
FIG. 9 is a longitudinal view of a blood filter device according to another embodiment, showing the filter deployed after insertion of the cannula into the aorta.

In another embodiment, a cannula is provided as depicted in FIGS. 6 and 7 with a continuous filter mesh as shown in FIG. 4 which extends beyond and over the lumen of the blood cannula so that blood from the cannula passes through the mesh before circulating within the patient. With reference to FIG. 9, the device may include a pressurizing cannula 300, blood cannula 350, inflation seal 317 and mesh 318. The device may optionally include a handle 380 and an inflation system as described above with reference to FIGS. 6 and 7. Moreover, the inflation system may be carried by either the pressurizing cannula or the blood cannula. In certain embodiments, the blood cannula and pressurizing cannula will be integrally combined into a single unitary component, and the inflation system may be carried either within or on the outside of the blood cannula. It will be understood that FIG. 9 shares many features in common with FIGS. 6 and 7, and the numbering of apparatus components has been duplicated so that appropriate description can be found with reference to FIGS. 6 and 7.

Figure 10:
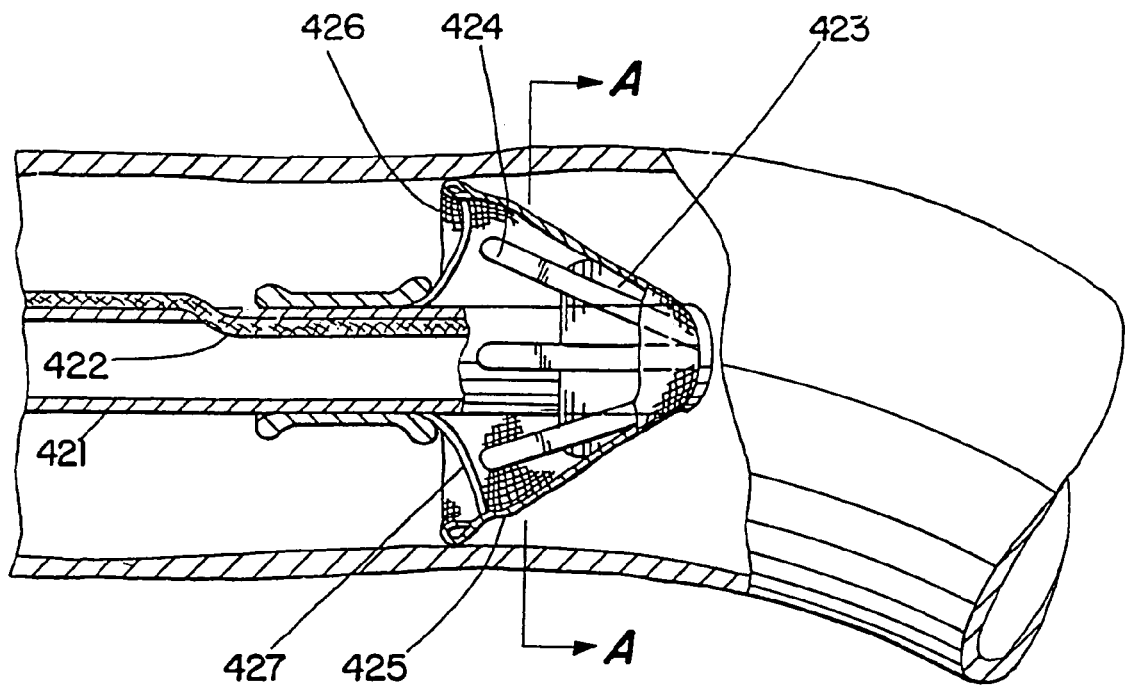
FIG. 10 is a longitudinal view of a blood filter device according to another embodiment.
Figure 10A:
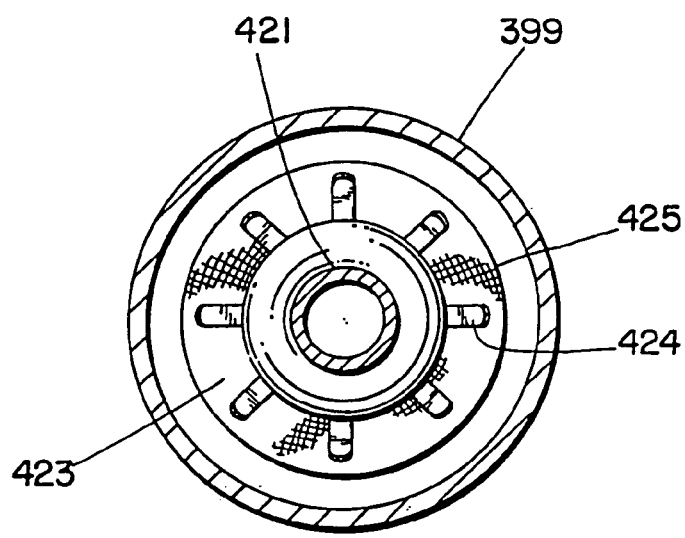
FIG. 10A is a cross-sectional view through section line I-I of the blood filter device depicted in FIG. 10.

In another embodiment, a cannula is provided with an inflatable loading balloon as depicted in FIG. 10. The device includes cannula 421 having pressurizing lumen 422 which extends from the proximal to the distal end. The cannula is equipped with an inflatable loading balloon 423 which, when inflated, exerts a radial outward force on stiffening wire ribs 424. The ribs support filtration mesh 425 which extends from the surface of the cannula at one edge to inflation seal 426 at another edge. A plurality of retrieving strings 427 are optionally provided which are attached at another end (not shown) to the plunger of the pressurizing syringe and therefore can be activated (advanced and withdrawn) by the motion of the pressurizing syringe which operates at the proximal end of cannula 421. Alternatively, the strings may be attached at the proximal end to a ring or slide which can be drawn to pull back, or advanced to let out the strings. FIG. 10A shows a cross-sectional view of aorta 399 taken through section line I-I. It can be seen that the cannula is equipped with a plurality of stiffening wire ribs 424 which extend radially outward when loading balloon 423 is expanded.

In another embodiment, a cannula with associated filter and distal flow diffuser is provided in FIGS. 11 and 11a. With reference to FIGS. 11 and 11a, the device includes a pressurizing cannula 300, blood supply cannula 350 and a blood filtration assembly 315 comprising holding strings 316 inflation seal 317, filter mesh 318, chamber 319, tubular passages 320 and 321, and septum 322. As shown in FIG. 11a the distal end of the blood supply cannula is closed with a cap 390 and the flow diffuser 395 is a rounded, hemispherical shape to facilitate the insertion of the distal end of the cannula 350 into the vessel. The flow diffuser 395 tapers towards the proximal end of the cannula 350 starting from the cap 390. The shape of the diffuser is preferably conical, in order to avoid damaging the blood. However, other shapes, including pyramidal shapes, may be employed.

In this FIGS. 11 and 11a embodiment, a plurality of outlet openings 391 are formed in the sidewall of the cannula 350 adjacent to its distal end. The openings may have an arched configuration, with the curved portion 392 of each arch oriented in the upstream direction. Although any number of openings are possible, a preferred embodiment has six openings. Preferably the total area of the openings is greater than the area of the distal end opening of a conventional catheter of the same diameter. The length of the openings 391 are also preferably greater than the length of the flow diffuser 395.

In another embodiment, a cannula with associated filter and flow diffuser is provided as depicted in FIGS. 12 and 12a. In this embodiment, the distal end of the cannula 350 contains a diffuser 396 with a helical configuration. The diffuser 396 can be held in place within the cannula by the tapering configuration of the distal end of the cannula, by adhesives, by ultrasonic welding, or by some other suitable means. The diffuser is preferably formed from a flat rectangular member with a single one-hundred-eighty degree twist. In this embodiment, the distal end of the cannula is partially blocked. Additionally, any number of outlet openings 397 may be formed in the sidewall of the cannula.

The intra-cannula flow diffusers of FIG. 11 and FIG. 12 may also be employed proximal to the filter by, for example, positioning the diffuser within the blood cannula of the device depicted in FIG. 9. Other variations and details of intra-lumen flow diffusers may be found in Cosgrove et. al., Low Velocity Aortic Cannula, U.S. Pat. No. 5,354,288, which is incorporated by reference herein.

Figure 13:
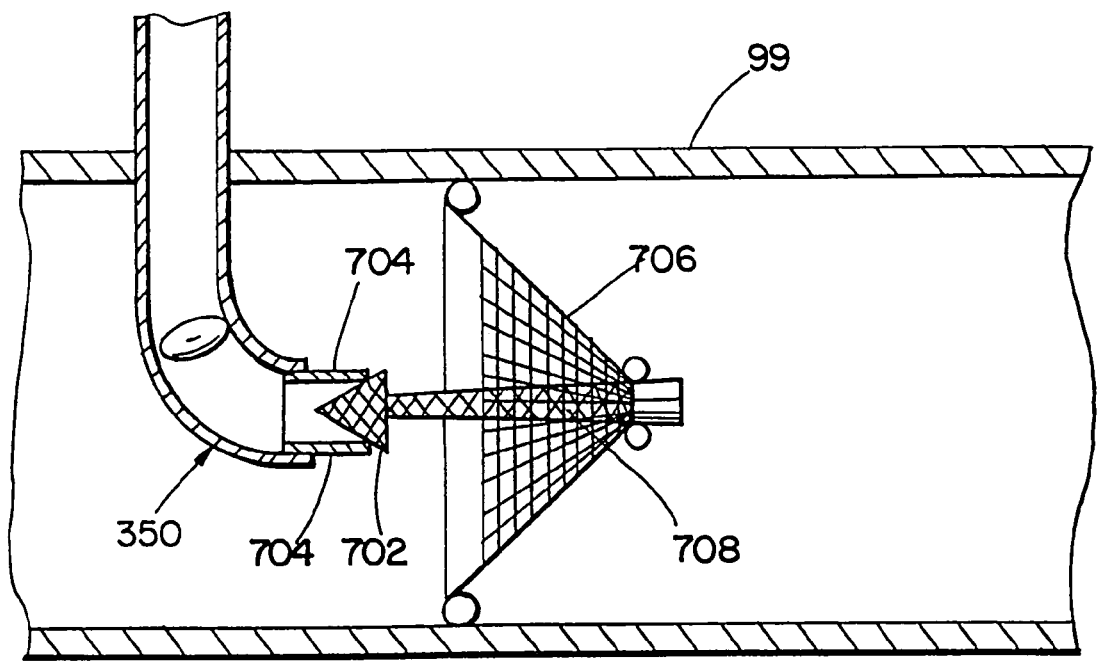
FIG. 13 is a longitudinal view of a cannula with associated filter and proximal flow diffuser.

In another embodiment, a blood cannula with associated filter and flow diffuser is provided as in FIG. 13. In this embodiment the proximal end of a flow diffuser 702 is connected to the distal end of the cannula 350 by a plurality of structural supports 704. The diffuser 702 is preferably conical, although other shapes may be used. The distal end of the flow diffuser 702 extends to the apex of the filter 706 by virtue of a linear shaft 708 said shaft running through the center of the expanded filter. In this embodiment the flow diffuser 702 diffuses blood flow proximal to the filter 706.

Figure 14:
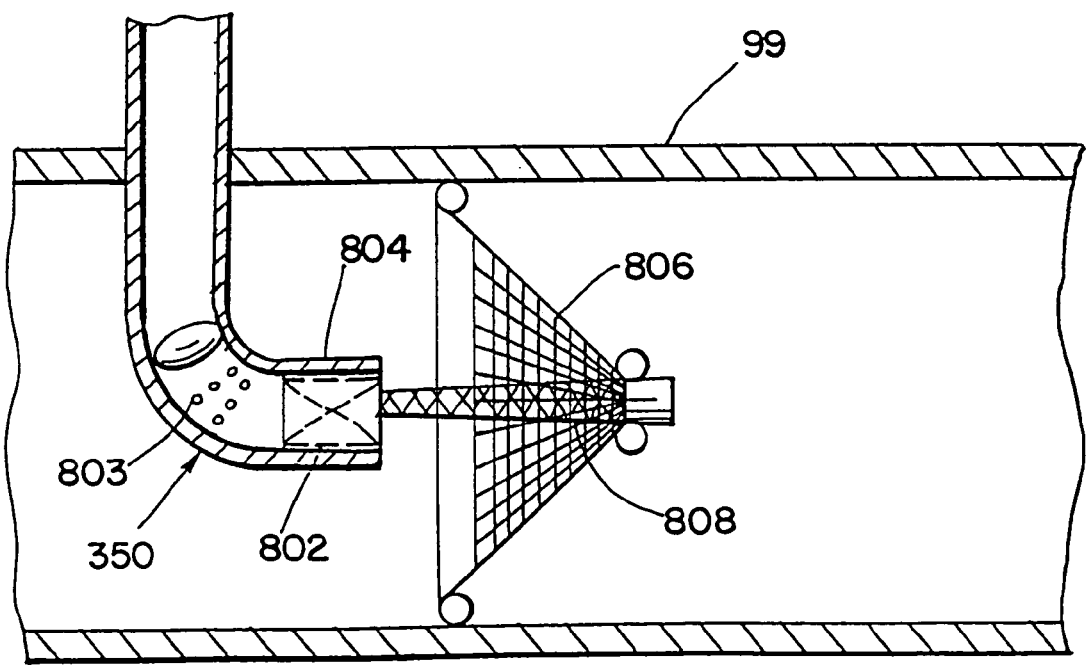
FIG. 14 is a longitudinal view of a cannula with associated filter and a proximal flow diffuser.

In another embodiment, an arterial blood cannula is provided as in FIG. 14. In this embodiment the flow diffuser 802 is contained within the distal end of the blood cannula 10. In a preferred embodiment, the diffuser 802 is the helical diffuser shown in FIGS. 12 and 12a. The flow diffuser 802 can be held in place by the tapering configuration of the distal end of the cannula, by adhesives, by ultrasonic welding, or by any other suitable means. Unlike the diffuser of FIG. 12, the distal end of the diffuser 802 is attached to the apex of the filter 806 by virtue of a linear shaft 808 said shaft running through the center of the expanded filter. The shaft may be any shape which will not traumatize blood components, and preferably comprises a rounded surface which tapers outward in the distal direction. In this embodiment the flow diffuser also diffuses cannula blood flow proximal to the filter. The cannula 350 optionally contains openings 803 in its distal end 804 to further diffuse the cannula blood. In an alternate embodiment, blood diffuser 802 is contained within cannula 350 but is not connected to filter 806 said filter being supported as disclosed in FIG. 9.

It is to be understood that flow diffusers such as those of FIG. 11-14 can be used in any blood filter device having a blood supply cannula and associated filter, including the devices depicted in FIG. 2 and FIG. 3. Furthermore, the diffuser of FIG. 14 may be employed inside a cannula having a distal filter, such as in FIG. 7, thus creating a blood filter device with two filters, one proximal to and one distal to the cannula opening.

Figure 15:
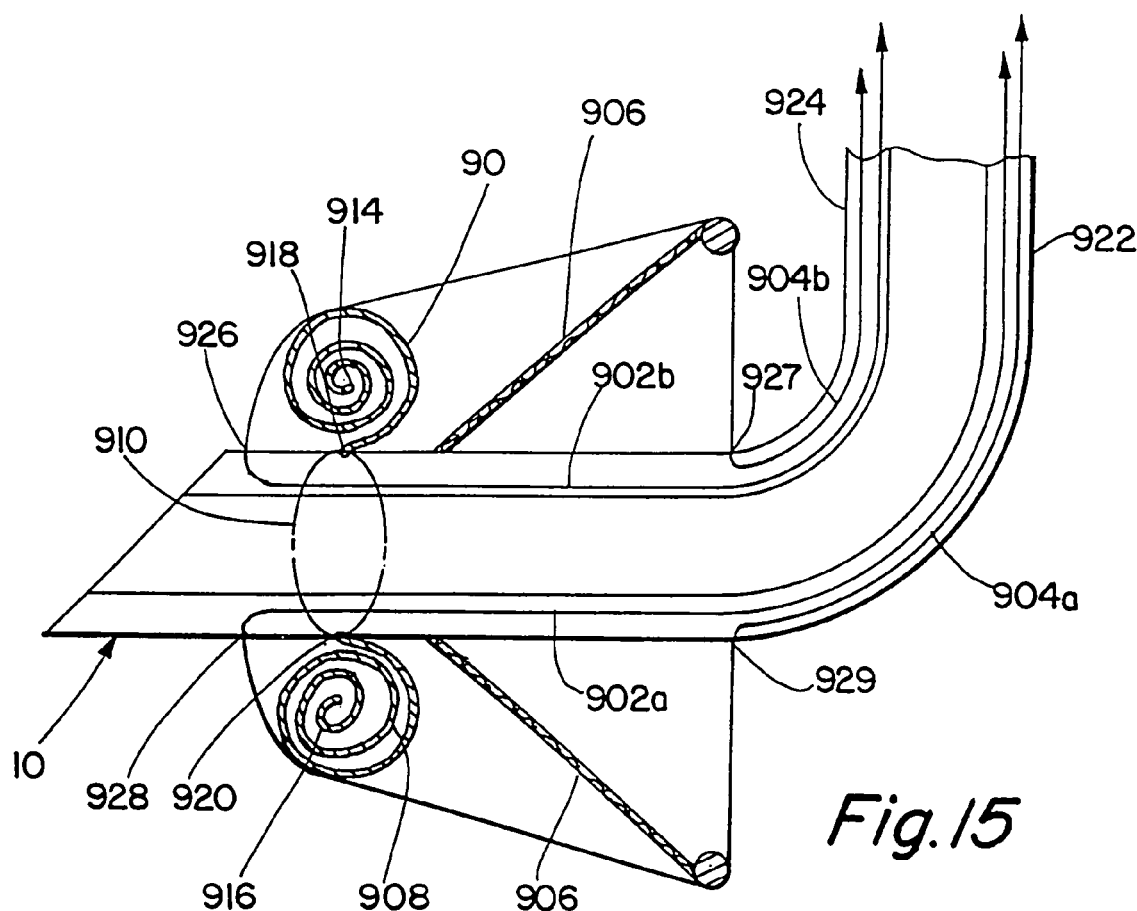
FIG. 15 is a longitudinal view of a cannula with associated filter according to another embodiment wherein the cannula includes a condom-like filter sleeve shown in a rolled back position.
Figure 16:
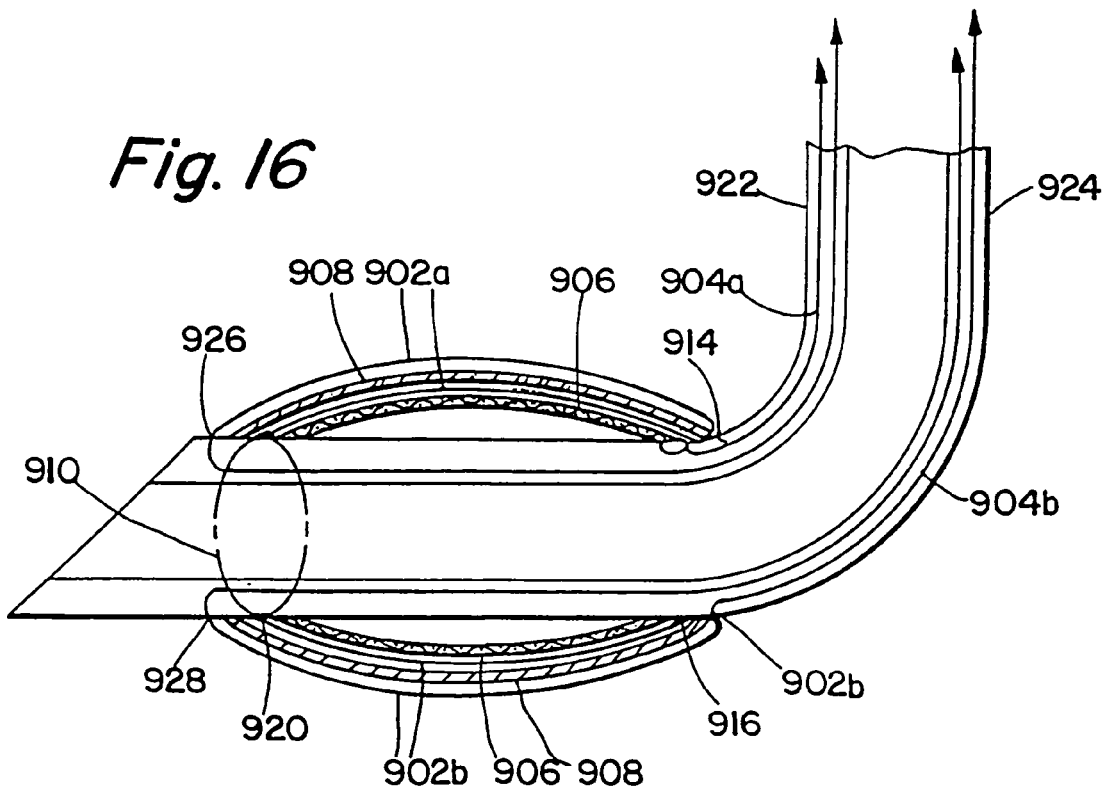
FIG. 16 is a longitudinal view of the cannula with associated filter of FIG. 15 wherein the unrolled filter sleeve has captured the filter assembly.

In an alternative embodiment, shown in FIG. 15, a blood filter device and associated filter 906 include a generally cylindrical filter sleeve 908 disposed circumferentially about the distal end of cannula 10, and attached to four control lines 902a, 902b, 904a, and 904b. Proximal force on unroll control lines 904a and 904b unrolls filter sleeve 908 from its depicted position so as to capture the filter as shown in FIG. 16. In this embodiment, the manner of unrolling the filter sleeve is analogous to the unrolling of a latex condom. Although the sleeve may be any shape, provided it both encases the device and rolls up in response to the control lines, in a preferred embodiment the sleeve has a circular cross-section.

In FIG. 15 the filter sleeve 908 is rolled back distal to the further to allow the filter to be fully expanded. FIG. 15 shows a cross-sectional cut-away of the sleeve. The full sleeve, not depicted, is a continuous piece surrounding the cannula about a 360 degree axis. In a preferred embodiment, a circular condom-like sleeve is attached at the outer-diameter of the cannula along the arc of circle 910. The condom-like sleeve has a distal opening to permit exit of the cannula tip. In a preferred embodiment a pair of control lines 902a and 904a enter a control lumen at points 928 and 929 respectively and run inside control lumen 922 adjacent the cannula lumen until exiting the control lumen at a proximal point on the cannula (not shown). In the preferred embodiment, control lines 902b and 904b similarly enter and exit a second control lumen 924 at points 926 and 927 respectively, said points located 180 degrees from the first lumen on the cannula's outer diameter.

As shown in FIG. 16, unroll control lines 904a and 904b are attached to sleeve 908 at points 914 and 916 respectively, said points located at the proximal end of the sleeve. Consequently, when sleeve 908 is rolled-up, as shown in FIG. 15, points 914 and 916 are rolled into the center of the nautilus-shaped lip of sleeve 908 while unroll control lines 904a and 904b are rolled-up along side the sleeve.

In contrast, roll-up control lines 902a and 902b are attached to the cannula at points 918 and 920 respectively. Points 918 and 920 are located on arc 910. When the sleeve is rolled-up as shown in FIG. 15 the roll-up control lines 902a and 902b run from their respective points of attachment 918 and 920, along the exposed side of the rolled-up sleeve, and enter the control lumens 922 and 924 at points 926 and 928 respectively. After entering the control lumens, the roll-up lines proceed through the control lumens until exiting at points (not shown) proximally located on the cannula.

FIG. 16 shows the same blood filter device with blood cannula and associated filter as FIG. 15 but with the sleeve 908 fully unrolled and capturing filter 906. The unrolled sleeve provides a compact, smooth profile for the device's introduction to and retraction from a vessel. In order to unroll the sleeve from the FIG. 15 position the unroll lines 904a and 904b of FIG. 16 are pulled in a proximal direction, away from the cannula tip. Consequently, points 914 and 916 are positioned at the proximal end of unrolled sleeve 908.

When the sleeve is in the unrolled state, the roll-up control lines 902a and 902b run from points 918 and 920 respectively, along the underside of the sleeve 908, around the proximal end of the sleeve, and then distally along the outer side of the sleeve before entering the control lumens 922 and 924 at points 926 and 928 respectively. After entering at points 926 and 928, the roll-up control lines 902a and 902b travel through the control lumens until exiting the control lumens at points (not shown) located at the proximal region of the cannula. When the sleeve is in the unrolled position as shown in FIG. 16, the roll-up lines may be pulled in a proximal direction, away from the cannula tip. Pulling the roll-up lines causes the sleeve 908 to roll-up until reaching the rolled-up state shown in FIG. 15. In a preferred method of use, the sleeve 908 is unrolled prior to insertion of the cannula in a vessel, rolled up during mesh deployment, and once again unrolled prior to cannula retraction.

Figure 17:
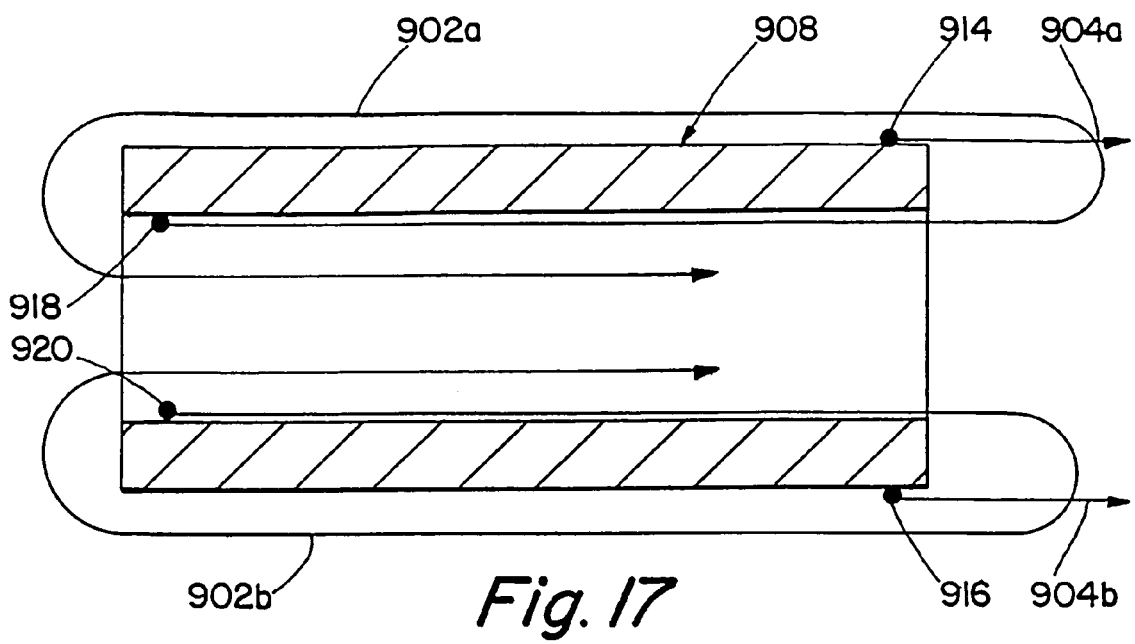
FIG. 17 shows detail of an unrolled filter sleeve and accompanying control lines.

FIG. 17 shows a cross-sectional detail of the sleeve 908 in the unrolled state, with emphasis on the points of attachment for the control lines. In the FIG. 17 embodiment, the sleeve, which is a continuous about 360 degrees (not shown), is directly connected to the two roll-up lines 902a and 902b at points 918 and 920 respectively. Alternatively, the roll-up lines are attached directly to the cannula at points neighboring 918 and 920 located immediately under the distal end of the sleeve. Pulling the roll-up lines in a proximal direction, as shown by the arrows in FIG. 17, causes the sleeve to roll-up like a condom. Accordingly, the sleeve material should be thin enough to avoid bunching and to provide smooth rolling in reaction to proximal force exerted by the roll-up lines. In a preferred embodiment, the sleeve is made of latex, with a thickness of between 3 and 14 thousandths of an inch. In a more preferred embodiment, the sleeve is made of latex with a thickness of between 4 and 16 thousandths of an inch. The invention may also use silicone or another silastic, biocompatible material to construct the sleeve. Other materials as are known in the art may permit use of a sleeve with a thickness of less than 6 thousandths of an inch provided the material gives suitable assurances against breaking or tearing.

Figure 18:
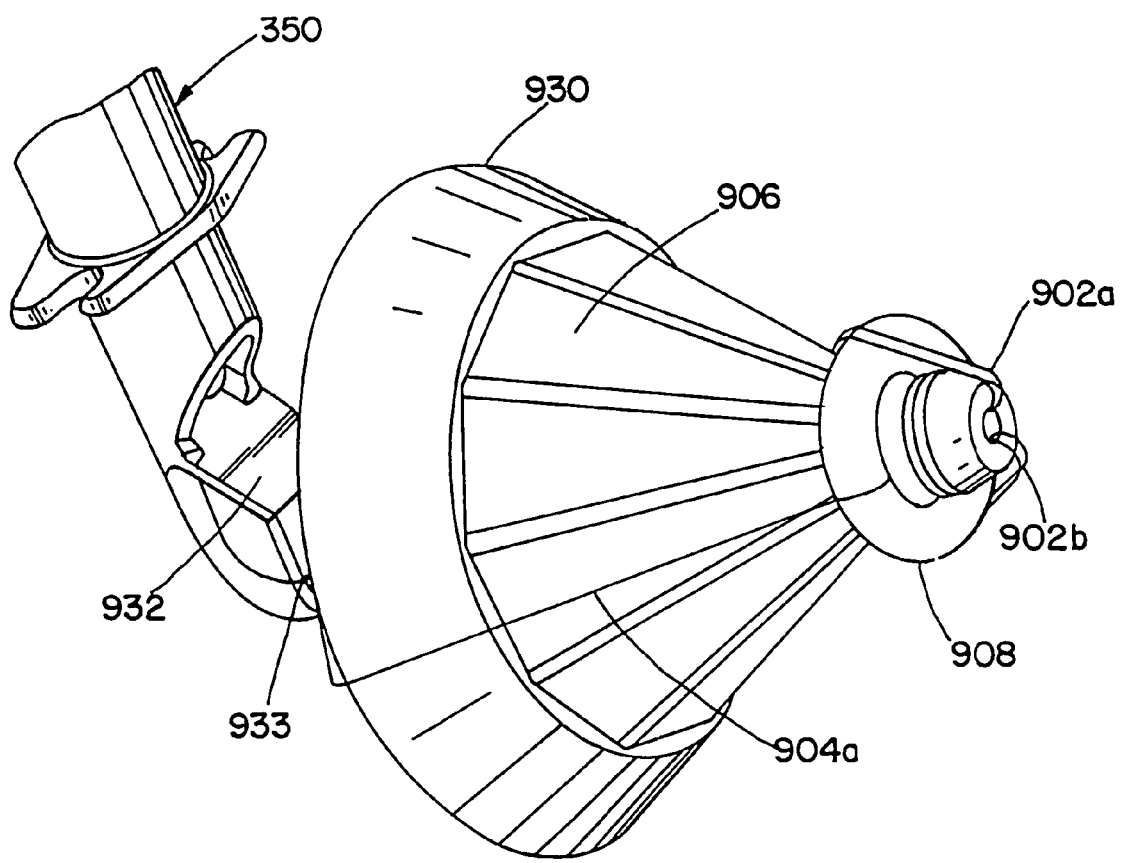
FIG. 18 is a three-dimensional drawing of a cannula with associated filter with a filter sleeve in the rolled up position.

FIG. 18 is a three-dimensional depiction of the cannula 350, filter 906 and sleeve 908, with sleeve 908 in the rolled-up state. In one embodiment, the filter 906 is located distal to the cannula opening such that cannula output is filtered upon exiting the cannula. In another embodiment the filter is located proximal to the cannula opening such that cannula output is downstream of the filter. The cannula opening may optionally have a planar diffuser 932. Filter 906 is made of a mesh which is contiguous with a sealing skirt 930. With the exception of entrance point 933 both the roll-up and unroll lines enter and exit the cannula at points not shown. In a preferred embodiment, the control lines attach to a control line actuating mechanism such as a capstan, ring or pulley (also not shown). In this embodiment, the structure adapted to open and close the filter may be an umbrella frame (not shown), such as depicted in FIG. 1, or alternatively an inflation balloon (not shown), such as shown in FIG. 7 and FIG. 9. The FIG. 18 embodiment may be used with any of the various means to actuate the structure as described herein.

Pulling unroll control lines 904a and 904b in a proximal direction causes the capture sleeve to roll out over the top of the filter. Subsequently pulling the roll-up control lines 902a and 902b in a proximal direction rolls-up the capture sleeve thereby permitting filter deployment. In FIG. 18, the unroll lines are oriented at an angle of 180 degrees from one another along the circumference of the filter (thus 904b not shown). The roll-up lines 902a and 902b are similarly oriented at an angle of 180 degrees from one another. However, as with the inventions of FIG. 15-17, this embodiment may employ any number of control lines spaced at varying differences around the outer diameter of the filter sleeve.

Figure 19:
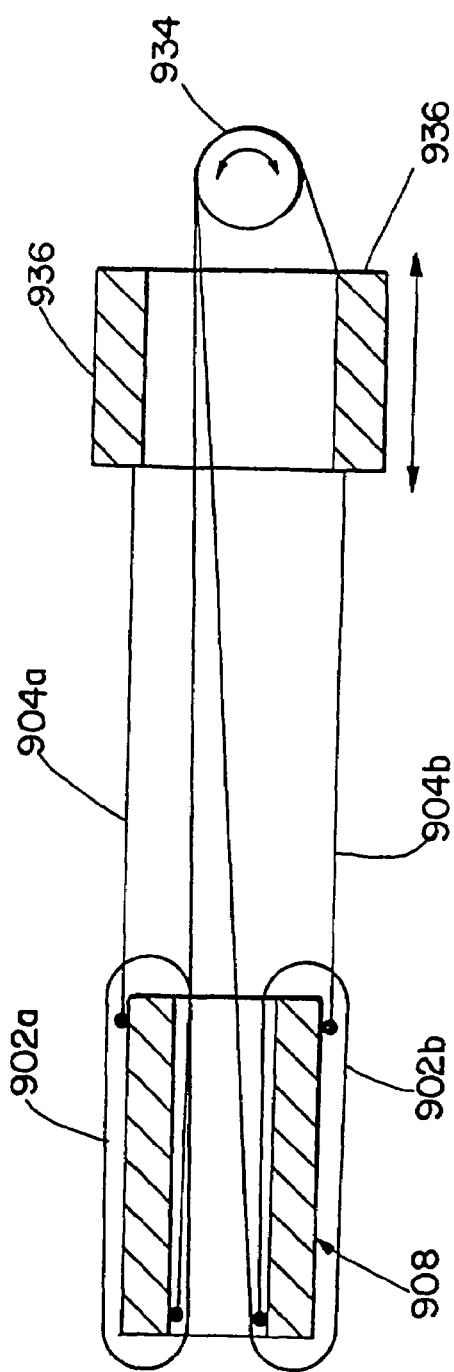
FIG. 19 is a longitudinal view of a cannula with associated filter including a sleeve deployable by virtue of a pulley mechanism.

FIG. 19 shows an alternative embodiment wherein one control ring 936 controls rolling and unrolling of the sleeve 934 with the assistance of a pulley mechanism. The control ring 936 is movable in both the proximal and distal directions along the outer diameter of the cannula (not shown). Control ring 936 is directly attached to unroll control lines 904a and 904b and attached to roll-up control lines 902a and 902b through pulley 934. Proximal movement of the control ring causes the sleeve 908 to unroll. Distal movement conversely causes sleeve 908 to roll up.

Figure 20:
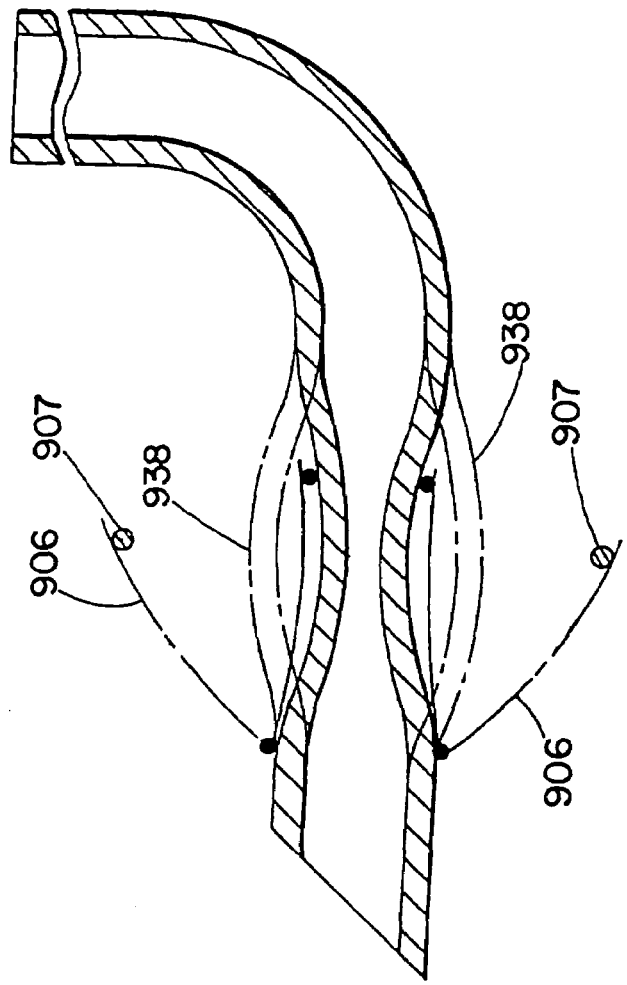
FIG. 20 is a longitudinal view of a cannula with associated filter wherein the cannula has a collapsible section which can accommodate the thickness of the filter.

In another embodiment of the blood filtration device, as shown in FIG. 20, the cannula 350 contains a collapsible or deformable section 938 such that the cannula can accommodate the filter 906 and filter seal 907, as well as other filter components. The collapsible section 938 is made out of an elastomeric material such as latex or silicone. In another embodiment the collapsible section is a double walled balloon. In a preferred embodiment the section is made of a flexible material with built in memory such that the collapsible walls automatically return to their non-collapsed state when deployment force expands the filter means. The collapsing section begins proximal to the filter seal 907 when the filter is in its collapsed state. In the embodiment shown, the collapsing section 938 begins just proximal to the site of the filter seal 907 and has a length equal to the length of the filter and filter seal. In an alternative embodiment, the collapsing section extends to the tip of the catheter from just proximal to the filter seal. The deformable section collapses radially inward when the filtration assembly is closed in order to produce a low-profile distal end to the cannula. Thus, a portion of the radial volume of the cannula is occupied by the filtration assembly when the filtration assembly is deployed; however, the blood flowing through the cannula subsequently blows the deformable cannula walls outwards to allow the flow of blood through the entire cannula diameter.

Figure 21:
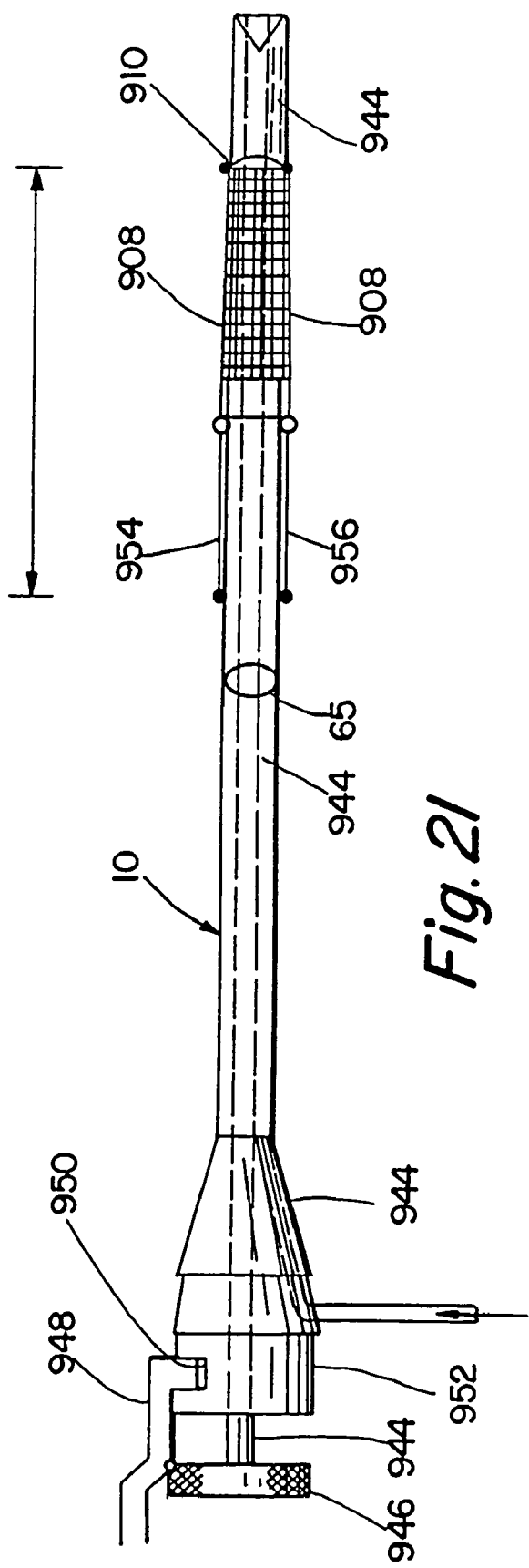
FIG. 21 is a longitudinal view of a balloon aortic elastic cannula wherein the cannula's outer diameter and filter profile are reduced by introduction of a stylet in the cannula's central lumen.
Figure 22:
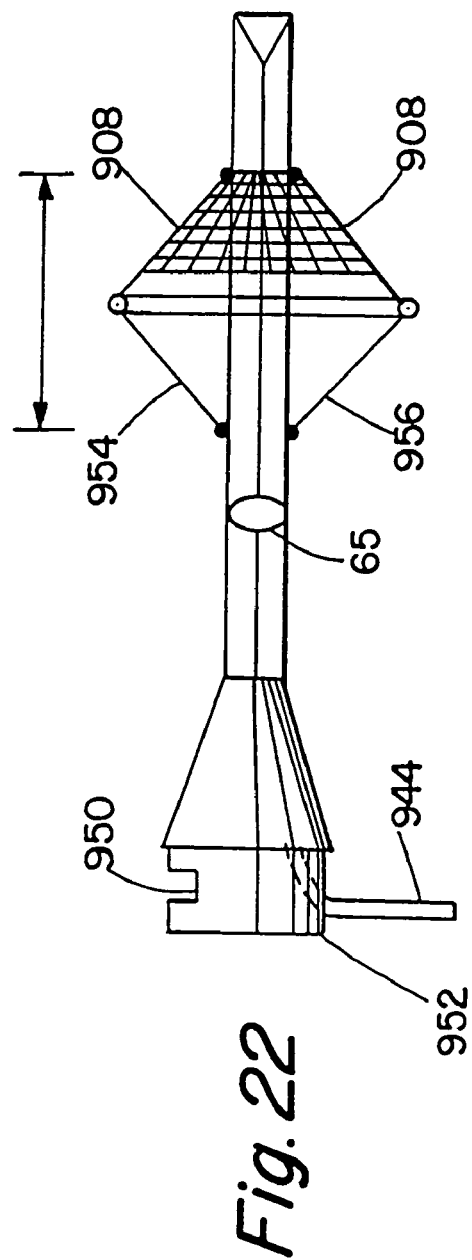
FIG. 22 is a longitudinal view of the balloon aortic elastic cannula of FIG. 21 wherein the stylet has been withdrawn.

In another embodiment of a blood filtration device, shown in FIGS. 21 and 22, the cannula 350 is composed of a medically acceptable elastic material, such as latex, silicone, rubber, and the like. As shown in FIG. 22, the cannula has an intrinsic length and diameter which characterizes the cannula when it is not under axial stress. The intrinsic length and diameter of the cannula vary according to vessel size. The cannula may be closed ended with a cap diffuser of the type disclosed in FIG. 11. Alternatively, the cannula may be partially closed at the tip as in FIG. 12.

As shown in FIG. 21, a stylet 944 is placed in the cannula 350 and engages the cannula tip. In an alternative embodiment, the stylet engages a ring suspended at the opening of an open tip. When inserted fully into the cannula, the lengthy stylet 944 engages the distal tip of the cannula and axially stretches the cannula body as shown. In this way the cannula is stretched so as to reduce cannula diameter. A finger grip 946 secured to the proximal end of the stylet includes latch member 948. The latch member engages a recess 950, formed on a proximal fitting 952 of the cannula, in order to maintain the cannula's stretched configuration. After insertion in the vessel, the elastic cannula is radially expanded and shortened by depressing latch member 948 and withdrawing the stylet as in FIG. 22.

In this embodiment, filter 908 is fixed to the outer diameter of the unexpanded elastic cannula 350 by tether lines 954 and 956 such that when the stylet is introduced cannula extension causes the tether lines to go taut. This in turn causes the filter to contour to the cannula. Conversely, as shown in FIG. 22, when the stylet is removed the cannula shortens thereby permitting expansion of the filter. Although various biasing and filter opening mechanisms may be used, in a preferred embodiment, the filter itself is made of memory-wire biased to an open state.

Figure 23:
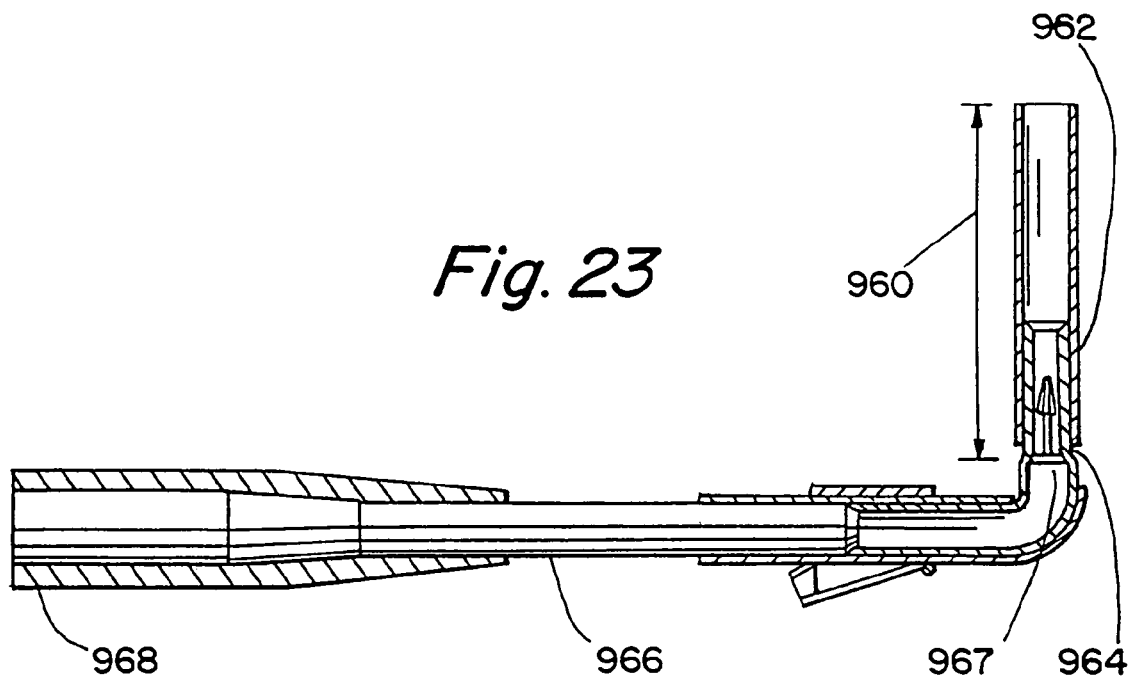
FIG. 23 is a longitudinal view of a cannula wherein the expander is proximal to the collapsible portion of the distal cannula.
Figure 24:
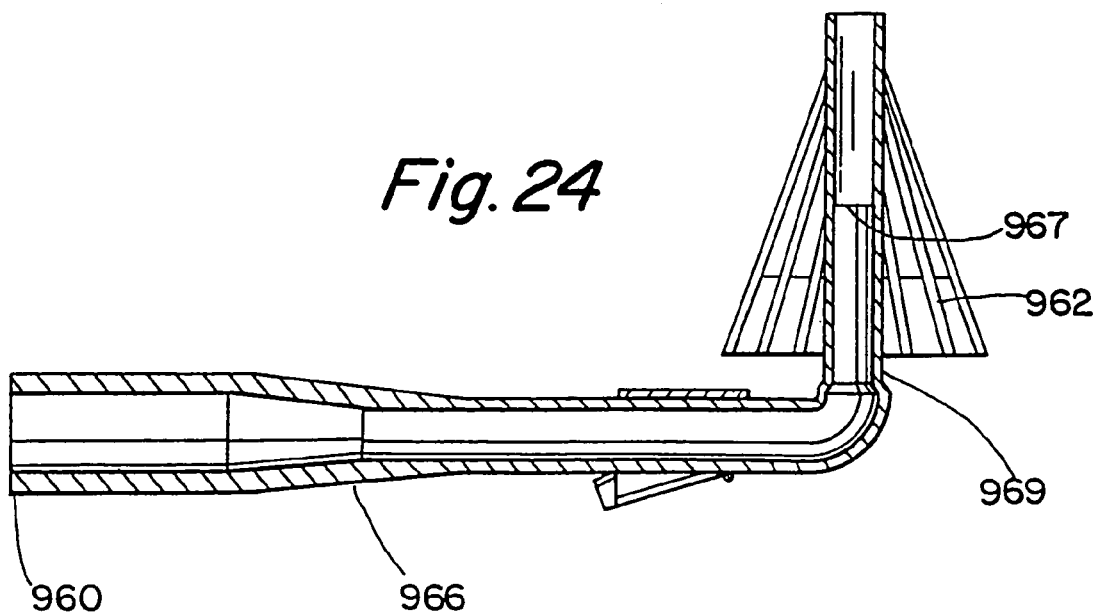
FIG. 24 is a longitudinal view of a cannula wherein the expander has been inserted into the collapsible portion of the distal cannula.
Figure 25:
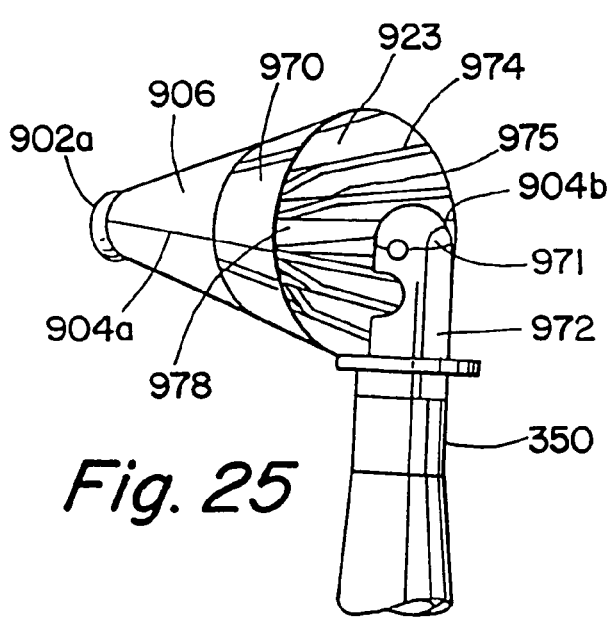
FIGS. 25 and 25c depict a cannula wherein the filter has an elasticmeric compliant edge which conforms to vessel irregularities.
Figure 25C:
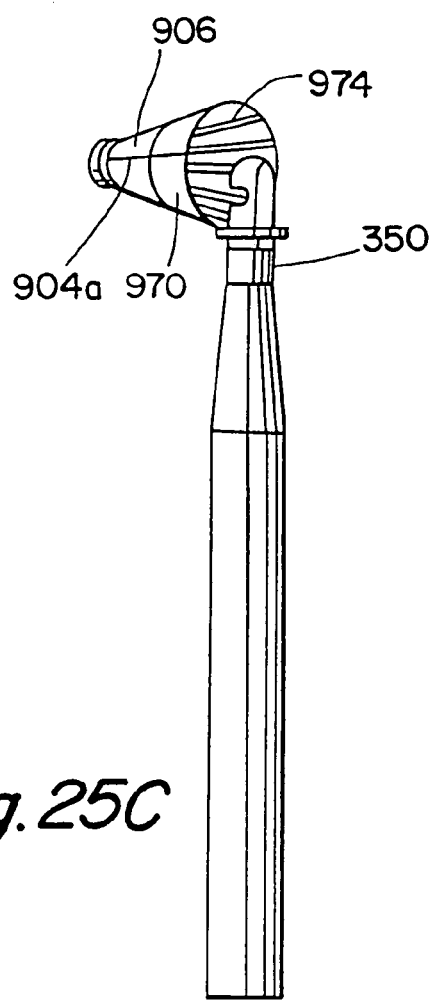
Figure 25D:
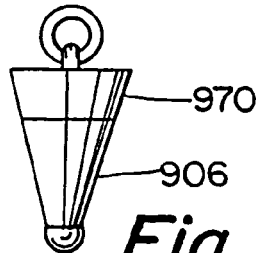
FIGS. 25a, 25b, and 25d show other views of the cannula depicted in FIG. 25c.
Figure 25A:
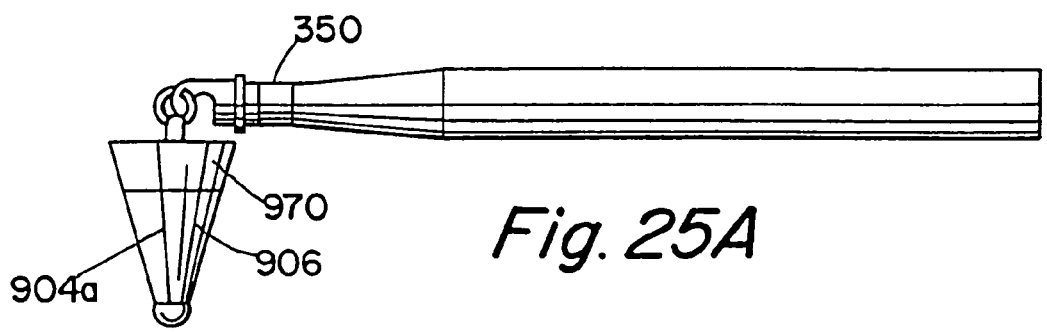
Figure 25B:
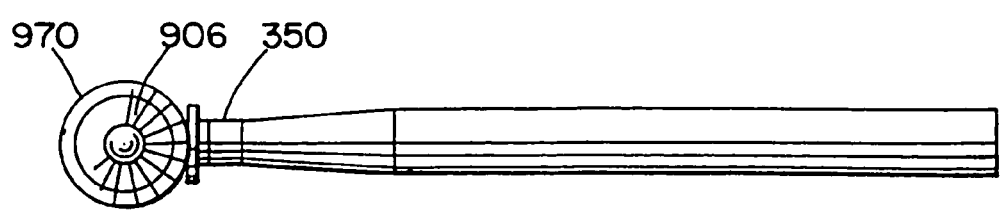

In another embodiment shown in FIGS. 23 and 24, the distal cannula portion 960 upon which the filter assembly 962 is mounted is, at least in part, a radially flexible material or composite construction which is normally in a necked down, contracted position. This allows the contracted filter assembly 962 to create as small of a profile as possible for insertion into the blood vessel. The necked-down portion 964 of the distal cannula is opened by inserting a close fitting expander 966 through the necked-down portion. The expander 966 has a distal end 967. As a result of the expander insertion, the filter assembly 962 exhibits an extruding profile relative to the outer contours of the distal cannula. Optionally as shown in FIG. 24, the filter assembly 962 may be fully deployed by a deployment mechanism (not shown), as previously described herein. In both FIGS. 23 and 24, the expander is fixed relative to the proximal cannula 968. Both are moved distally relative to the distal cannula so as to insert the expander into the collapsible section. Alternatively, the expander 966 may move independent of the proximal cannula 968.

In another embodiment shown is FIGS. 25 and 25A to 25D, cannula 350 includes filter 906 having skirt 970 disposed around its outermost edge. Skirt 970 is an elasticmeric strip of material (e.g., silicon or other suitable material) attached to the proximal edge of the filter mesh. Skirt 970 forms a compliant edge which conforms to vessel lumen topography and gives a better seal with the vessel lumen when the filter is deployed. Moreover, the compliant edge 970 allow for changes in the vessel interior dimension as the vessel pulses from systole to diastole. Both unroll control lines 904a and 904b, as well as roll-up control lines 902a and 902b (not shown) are routed through tube 978 and then through the cannula housing at location 971 and thereafter ride within tubing 972 to the point where they are manipulated outside of the body. In addition to the roll-up and unroll control lines, a fifth control line is also carried through tube 972 and location 971 for the purpose of operating the umbrella frame 973 depicted in FIG. 25. This control line can ride either inside or outside of tube 978. The umbrella frame consists of a series of primary struts 974 extending from the distal to proximal end of the mesh and disposed circumferentially thereabout, and a series of secondary struts 975. Struts 975 connect at their proximal end to struts 974 and at their distal end are slideably connected to the axis of the conical filtration mesh. Secondary struts 975 therefore operate to open and close the expansion frame between a radially expanded and radially contracted condition.

Figure 26:
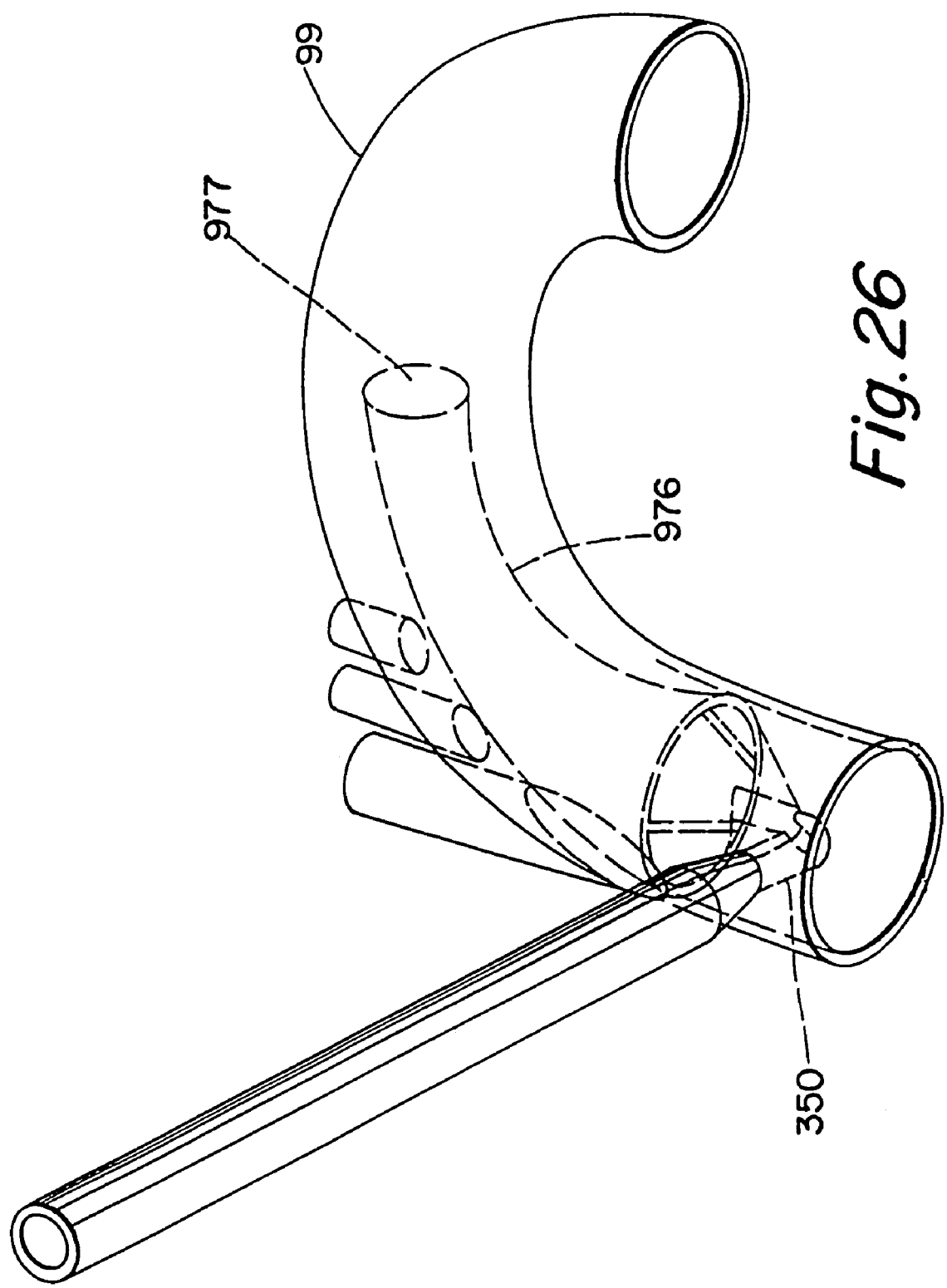
FIG. 26 shows a cannula having an open-ended sleeve disposed within the aorta.

In another embodiment shown in FIG. 26, cannula 350 includes on its distal end a "windsock" or open-ended sleeve 976 which is either a porous mesh, a non-porous material (e.g., silicon), or a non-porous material with holes which allow some degree of lateral blood flow. In FIG. 26, the windsock cannula is shown deployed within aorta 99. As can be seen, embolic debris dislodged upstream of the cannula will be carried through the windsock 976 and will exit the distal opening 977. Sleeve 976 thereby prevents passage of embolic material laterally in the region of the carotid arteries and thereby prevents or reduces the occurrence of embolic material reaching the brain. At the same time, however, the windsock apparatus overcomes difficulties associated with filter blockage due to blood clotting and buildup of debris by delivering a high volume of blood downstream of the carotid arteries without the need to pass laterally through the sleeve.

In another embodiment, a filter is provided in the form of a "lobster trap" as depicted in Reger et al., U.S. Pat. No. 5,108,419 (FIGS. 2, 14, 15) and U.S. Pat. No. 5,160,342, incorporated herein by reference. A filter of this construction allows debris into an entrapment chamber through a small opening. A series of other small openings generally are included within this structure, and debris therefore advances one-way, distally through the structure. However, once the material enters the structure it cannot get out, and thus, if there is a momentary reversal of blood flow within the vessel, embolic debris cannot wash away from the filter.

It is to be understood that the blood filtration devices of FIG. 15-FIG. 26, as well as the lobster trap, may optionally employ any elongated insertion member in place of blood cannula 350. The elongated insertion member need not contain a lumen.

As a purely illustrative example of one of the methods of filtering blood as disclosed herein, the method will be described in the context of cardiac bypass surgery as described in *Manual of Cardiac Surgery, d. Ed.*, by Bradley J. Harlan, Albert Spar, Frederick Harwin, which is incorporated herein by reference in its entirety.

A preferred method of the present invention may be used to protect a patient from embolization during cardiac surgery, particularly cardiac bypass surgery. This method includes the following steps: introducing a mesh into an aorta of the patient; positioning the mesh to cover substantially all of the cross-sectional area of the aorta preferably proximal to the carotid arteries so that the mesh may entrap embolic matter or foreign matter in the blood before it can escape to the brain; adjusting the mesh to maintain its position covering substantially all of the cross-sectional area of the aorta; and removing the mesh and the entrapped foreign matter from the aorta. A variant comprises placing a cylindric mesh at the level of the take off of the cerebral vessel to divert emboli otherwise destined for the brain to other parts of the body.

During the cardiac surgery, the aorta is clamped a number of times. Because clamping the aorta dislodges atheromatous material from the walls of the aorta, which is released into the bloodstream, the mesh must be positioned within the aorta before clamping begins. Atheromatous material also accumulates behind the clamps during the surgery and, because removal of the clamps releases this material into the bloodstream, the mesh must be maintained within the blood stream for about four to ten minutes after removal of the clamps. Because the aorta is often a source of much of the atheromatous material that is eventually released into the bloodstream, it is preferable to place the mesh in the aorta between the heart and the carotid arteries. This placement ensures that foreign matter will be entrapped before it can reach the brain.

For illustration purposes, the method for filtering blood will be described in connection with the device depicted in FIG. 4. After a patient has been anaesthetized and the patient's chest has been opened in preparation for the bypass surgery, the cannula 205, ranging from about 22 to about 25 Fr.O.D. in size, is introduced into an incision made in the aorta. The cannula 205 is sutured to the aortic wall, and the heart is paralyzed. The device 10 is stored in a closed position within the cannula 205, in which the balloon 230 is deflated and folded in upon itself, and the mesh 220 is closed. The cannula 205 and the device 10 will not interfere with other equipment used in the surgical procedure.

The blood filter device 10 is then inserted into the aorta through the cannula 205 via the tie lines 250. Saline is introduced into the balloon 230 through the actuation assembly 260 from an extracorporeal reservoir, and the device 10 gradually assumes an open position in which the balloon 230 is inflated in a donut-shape and the mesh 220 is opened to cover substantially all of the cross-sectional area of the vessel. In the opened position, the device 10 is ready to entrap foreign matter in the blood flow. By adjusting the amount of saline introduced into the balloon 230, the surgeon may control the amount of inflation and consequently the degree to which the mesh 220 is opened. After the device 10 has been actuated, blood from a bypass machine is introduced into the aorta through the cannula 205 and is filtered by the device 10.

To block the flow of blood back into the heart, the surgeon cross-clamps the aorta, or, in an alternative procedure, balloon occludes the artery or aorta. Cross-clamping and/or balloon occluding the aorta dislodges atheromatous material from the walls of the aorta and releases it into the blood flow. Because cross-clamping is done upstream from the device 10, the atheromatous material will be filtered from the blood by the device 10. While the aorta is cross-clamped, the surgeon grafts one end of a vein removed from the patient's leg on to the coronary artery. After the surgeon checks the blood flow to make sure there is no leakage, the aortic clamps are removed. Atheromatous material accumulates behind the clamps and, when the clamps are removed, this material is released into the blood flow, which will be filtered by the device 10. The flow rate from the bypass machine is kept low to minimize embolization, and the heart is made to beat again.

During surgery, the position of the mesh may require adjustment to maintain its coverage of substantially all of the cross-sectional area of the aorta. To accomplish this, the surgeon occasionally palpates the outside of the aorta gently in order to adjust the device 10 so that the mesh 220 covers substantially all of the cross-sectional area of the aorta. The surgeon may also adjust the location of the device 10 within the aorta.

The device 10 may also be used in conjunction with TCD visualization techniques. Through this technique, the surgeon may actuate the device 10 only when the surgeon expects a flurry of emboli such as during aortic cannulation, inception, and termination of bypass, aortic clamping, and clamp release.

The surgeon then clamps the aorta longitudinally to partially close the aorta, again releasing the atheromatous material to be filtered by the device 10. Holes are punched into the closed off portion of the aorta, and the other end of the vein graft is sewn onto the aorta where the holes have been punched. The aortic clamps are then removed, again releasing accumulated atheromatous material to be filtered from the blood by the device 10. The surgeon checks the blood flow to make sure there is no leakage. The heart resumes all the pumping, and the bypass machine is turned off, marking the end of the procedure.

The saline is then removed from the balloon 230 via the actuation assembly 260, deflating the balloon 230 and closing the mesh 220 around the entrapped emboli. The device 10 is then retracted into the cannula 205 by pulling the tie lines 250 into the cannula 205. If the balloon 230 has not been deflated sufficiently before retraction, excess saline may be squeezed out of the balloon 230 as it is retracted into the cannula 205. Finally, the cannula 205 and the device 10, along with the entrapped emboli, are removed from the body. Because the device 10 is in place throughout the procedure, any material released during the procedure will be entrapped by the device 10.

When the device 10 is used in conjunction with other invasive procedures, the dimensions of the device should be adjusted to fit the vessel affected. An appropriate mesh also should be chosen for blood flow in that vessel. In use, the device may be positioned so that it is placed downstream of the portion of the vessel that is affected during the procedure, by clamping or other step in the procedure. For example, in order to entrap emboli material in a leg artery, the cone-shaped filter can be placed such that the cone points toward the foot.

An advantage of the devices and methods of the present invention and the methods for filtering blood described herein is that it is possible to entrap foreign matter resulting from the incisions through which the devices are inserted. Another advantage of the devices of the present invention is that the flexibility of the inflatable balloon allows it to conform to possible irregularities in the wall of a vessel.

In other methods of the invention, the filter is decoupled from the cannula and the filter is disposed on an elongate member separate from the cannula. As such, while the cannula is inserted into the aorta generally upstream of the aortic arch, the filter disposed on an elongate member may or may not be entered through the same incision as the cannula. Thus, the filter may enter by any of the following routes; (1) through the cannula and deployed downstream of the cannula, (2) through the cannula and deployed upstream of the cannula, (3) through the left subclavian artery and deployed at a point either upstream or downstream of the cannula, and (4) through the femoral artery and thereafter into the aortic arch and deployed either upstream or downstream of the cannula. In other methods of the invention, the filter is deployed during stages of the cardiac surgery procedure and removed between certain stages.

The cerebral embolic signals during coronary artery bypass grafting are as follows (expressed as percentage embolic release per event): cannula on=2%, bypass on=6%, aortic cross clamp on=6%, aortic cross clamp off=21%, partial occlusion clamp on=7%, partial occlusion off=14%, bypass off=8%. Moreover, during the approximately 5.8 minute interval between bypass on and aortic cross clamp on, approximately 4% of embolic material is released. During the approximately interval between placement of the cross clamp and removal of the aortic cross clamp, a time of approximately 38.8 minutes, about 13% of the embolic material is released. During the approximately 4.1 minute interval between removal of the aortic cross clamp and installation of the partial occlusion clamp, approximately 9% of embolic material is released. During the approximately 9.7 minute interval between placement of the partial occlusion clamp and removal of the partial occlusion clamp, approximately 2% of embolic material is released. Finally, during the 7.3 minute interval between removal of the partial occlusion clamp and turning bypass off, approximately 8% of embolic material is released.

Thus, in one embodiment, it is desirable to have a filter deploy shortly before cross clamp removal and removed shortly thereafter. In another embodiment, it is desirable to have a filter deploy only during the period just after cross clamp placement and removed after cross clamp removal. In still another embodiment, it is desirable to have the filter deployed just before placement of the aortic cross clamp and maintained until after removal of the aortic cross clamp. Alternatively, the filter may be deployed before and removed after installation of the cross clamp or removal of the cross clamp or placement of the partial occlusion clamp or removal of the partial occlusion clamp. In still another embodiment, the filter is deployed only during the interval between placement and removal of the aortic cross clamp. Thus, in some embodiments it will be desirable to have the filter deployed only transiently for events of short duration, e.g., cannula on, bypass on, cross clamp on, cross clamp off, partial occlusion clamp on, partial occlusion clamp off, and bypass off. In other embodiments, it will be desirable to have the filter deployed throughout a number of these manipulative events. In still other embodiments it will be desirable to have the filter deployed only during one. or more interval between these manipulative events. For a discussion of embolic staging during bypass surgery the reader is referred to Barbut et al., *Stroke* 25:2398-2402 (1994), expressly incorporated herein by reference.

While particular devices and methods have been described for filtering blood, once this description is known, it will be apparent to those of ordinary skill in the art that other embodiments and alternative steps are also possible without departing from the spirit and scope of the invention. Moreover, it will be apparent that certain features of each embodiment can be used in combination with devices illustrated in other embodiments. For example, the inflation system illustrated in FIG. 7 can be used with any of the devices depicted in FIGS. 1-4. Accordingly, the above description should be construed as illustrative, and not in a limiting sense, the scope of the invention being defined by the following claims.

What is claimed is:

1. A restraining mechanism configured to prevent a plurality of struts of a filter device from extending outwardly prior to deploying a filter of the filter device, the restraining mechanism comprising:
    (a) a sleeve adapted to be disposed substantially at a distal end of the filter device, said sleeve being adapted to unroll and apply a restraining force to the plurality of struts of the filter device to prevent the plurality of struts from extending outwardly; and
    (b) at least one actuating member coupled to said sleeve, said at least one actuating member being adapted to release said restraining force of said sleeve and enable the plurality of struts of the filter device to extend outwardly.

2. A restraining mechanism as recited in claim 1, wherein said at least one actuating member is adapted to cause said sleeve to unroll in a proximal direction upon moving said at least one actuating member in said proximal direction.

3. A restraining mechanism as recited in claim 1, wherein said sleeve is coupled to at least two of said plurality of struts.

4. A restraining mechanism as recited in claim 1, wherein said sleeve comprises at least one preferential separation region.

5. A restraining mechanism as recited in claim 4, wherein said at least one actuating member cooperates with said at least one preferential separation region and is adapted to preferentially separate said sleeve at said at least one preferential separation region.

6. A restraining mechanism configured to prevent a plurality of struts of a filter device from extending outwardly prior to deploying a filter of the filter device, the restraining mechanism comprising:
    (a) rolling means for applying a restraining force to the plurality of struts of the filter device to prevent the plurality of struts from extending outwardly, said rolling means for apply the restraining in force being oupled to at least one of the plurality of struts; and
    (b) at least one actuating member cooperating with said rolling means for applying the restraining force, of said at least one actuating member being adapted to release said restraining force of said rolling means for applying said restraining force and enable the plurality of struts of the filter device to extend outwardly to deploy the filter.

7. A restraining mechanism as recited in claim 6, wherein said means for applying the restraining force comprises a sleeve attached to each of said plurality of struts, said sleeve comprising at least one preferential separation region.

8. A restraining mechanism as recited in claim 7, wherein said at least one actuating member cooperates with said at least one preferential separation region, said at least one actuating member being adapted to cause said means for applying the restraining force to preferentially separate at said at least one preferential separation region.

9. A restraining mechanism as recited in claim 6, wherein said means for applying the restraining force comprises a sleeve substantially surround the plurality of struts.

10. A restraining mechanism as recited in claim 9, wherein said sleeve is adapted to roll in a proximal direction upon moving said actuating member in the proximal direction.

11. A restraining mechanism as recited in claim 10, wherein said sleeve is a polymer sleeve.

* * * * *